(12) United States Patent
Zheng et al.

(10) Patent No.: US 9,493,501 B2
(45) Date of Patent: Nov. 15, 2016

(54) METHYLTRANSFERASE INHIBITORS FOR TREATING CANCER

(71) Applicant: MEMORIAL SLOAN-KETTERING CANCER CENTER, New York, NY (US)

(72) Inventors: Weihong Zheng, New York, NY (US); Minkui Luo, New York, NY (US); Glorymar del Valle Ibanez Sanchez, Corona, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 223 days.

(21) Appl. No.: 14/353,815

(22) PCT Filed: Oct. 26, 2012

(86) PCT No.: PCT/US2012/062157
§ 371 (c)(1),
(2) Date: Apr. 24, 2014

(87) PCT Pub. No.: WO2013/063417
PCT Pub. Date: May 2, 2013

(65) Prior Publication Data
US 2014/0303106 A1    Oct. 9, 2014

Related U.S. Application Data

(60) Provisional application No. 61/551,976, filed on Oct. 27, 2011, provisional application No. 61/552,236, filed on Oct. 27, 2011, provisional application No. 61/624,636, filed on Apr. 16, 2012.

(51) Int. Cl.
*C07H 19/14* (2006.01)
*C07H 19/16* (2006.01)
*C07D 473/34* (2006.01)
*C07D 487/04* (2006.01)

(52) U.S. Cl.
CPC ............. *C07H 19/14* (2013.01); *C07D 473/34* (2013.01); *C07D 487/04* (2013.01); *C07H 19/16* (2013.01)

(58) Field of Classification Search
None
See application file for complete search history.

(56) References Cited

U.S. PATENT DOCUMENTS

2008/0132525 A1*  6/2008  Wahhab ............... C07D 471/04
                                                        514/263.4

FOREIGN PATENT DOCUMENTS

WO      2009153575 A1    12/2009

OTHER PUBLICATIONS

Patani, G. A. et al., Chemical Review, "Bioisosterism: A Rational Approach in Drug Design", 1996, vol. 96, pp. 3147-3176.*
Zips, D. et al., In Vivo, "New Anticancer Agents: In Vitro and In Vivo Evaluation", 2005, vol. 19, pp. 1-8.*
Weihong Zheng et al; "Sinefungin Derivatives as Inhibitors and Structure Probes of Protein Lysine Methyltransferase SETD2," Journal of the American Chemical Society, vol. 134, No. 43, Oct. 31, 2012, pp. 18004-18014.
Osborne Tanesha C et al; "Protein arginine methyltransferase 1: Positively charged residues in substrate peptides distal to the site of methylation are important for substrate binding and catalysis," Biochemistry, American Chemical Society, US, vol. 46, No. 46, Nov. 1, 2007, pp. 13370-13381.
Shuichi Mori, Kenta Iwase, Naoko Iwanami et al.; "Development of novel bisubstrate-type inhibitors of histone methyltransferase SET7/9," Bioorganic & Medicinal Chemistry, vol. 18, Oct. 14, 2010, pp. 8158-8166.
Spannhoff A et al; "Cancer treatment of the future: Inhibitors of histone methyltransferases," International Journal of Biochemistry and Cell Biology, Pergamon, GB, vol. 41, No. 1, Jan. 1, 2009, pp. 4-11.

(Continued)

*Primary Examiner* — Shaojia Anna Jiang
*Assistant Examiner* — Bahar Craigo
(74) *Attorney, Agent, or Firm* — Heslin, Rothenberg, Farley & Mesiti P.C.

(57) ABSTRACT

Compounds having methyltransferase inhibitory activity are disclosed. The compounds have the structure

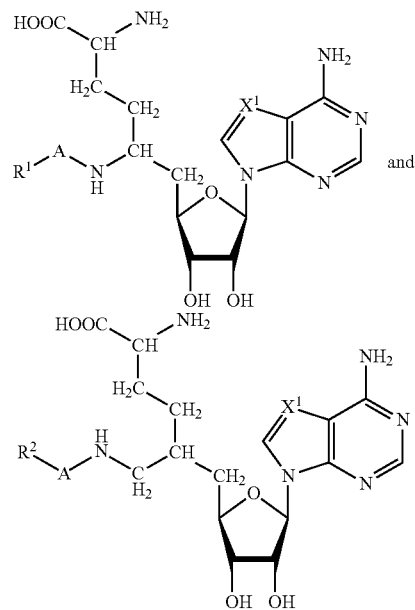

and are useful in the treatment of cancer and similar diseases associated with inappropriate methyltransferase activity.

13 Claims, No Drawings

(56) References Cited

OTHER PUBLICATIONS

International Search Report for PCT/US2012/062157 dated Jan. 24, 2013.
Xueqiang Yin et al; "Carbocyclic sinefungin," Tetrahedron Letters vol. 48, 2007, pp. 4809-4811.
Arun K. Ghosh et al; "Total Synthesis of (+)-Sinefungin," J. Org. Chem., vol. 61, 1996, pp. 6175-6182.
Robert A. Copeland et al; "Protein methyltransferases as a target class for drug discovery," Nature Reviews|Drug Discovery, vol. 8, Sep. 2009, pp. 724-732.
Guoxia Zhao; "Synthetic explorations to sinefungin analogs," Dissertation Abstract, Auburn University, May 9, 2009, 173 pages.
Tetyana S. Shulyak; "Exploring sinefungin analogs as potential antiviral agents," Dissertation Abstract, Auburn University, Aug. 8, 2005, 159 pages.
James Dowden et al; "Toward the development of potent and selective bisubstrate inhibitors of protein arginine methyltransferases," Bioorganic & Medicinal Chemistry Letters 20, 2010, pp. 2103-2105.
Jose Maria et al; Eur. J. Org. Chem., 2000, pp. 627-631.
Wenyu Yu et al; "Catalytic site remodeling of the DOT1L methyltransferase by selective inhibitors," Nature Communications|3:1288, Dec. 18, 2012, pp. 1-11.
Scott R. Daigle et al; "Selective killing of mixed lineage leukemia cells by a potent small-molecule DOT1L inhibitor," Cancer Cell 20, Jul. 12, 2011, pp. 53-65.
Justin L. Anglin et al; "Synthesis and structure—Activity relationship investigation of adenosine-containing inhibitors of histone methyltransferase," Journal of Medicinal Chemistry, vol. 55, 2012, pp. 8066-8074.

\* cited by examiner

METHYLTRANSFERASE INHIBITORS FOR TREATING CANCER

CROSS REFERENCE TO RELATED APPLICATIONS

This application is a national phase filing under 35 U.S.C. §371 of PCT International Application PCT/US2012/062157, filed Oct. 26, 2012, and published under PCT Article 21(2) in English as WO 2013/063417 on May 2, 2013. PCT/US2012/062157 claimed claims priority from U.S. provisional applications 61/551,976; 61/552,236; and 61/624,636; filed Oct. 27, 2011; Oct. 27, 2011; and Apr. 16, 2012, respectively. The entire contents of all three are incorporated herein by reference.

FIELD OF THE INVENTION

The invention relates to chemical compounds having methyltransferase inhibitory activity and their use in the treatment of diseases and conditions associated with inappropriate methyltransferase activity.

BACKGROUND OF THE INVENTION

Epigenetics is inheritable information not encoded in DNA manifested through control of gene expression, thereby controlling a range of cellular activity, including determining cell fate, stem cell fate and regulating proliferation. Epigenetic control over gene expression is accomplished in at least four ways: (1) covalent histone modification, (2) covalent DNA modification, (3) histone variation, and (4) nucleosome structure and DNA/histone contact points. Epigenetic control through one mechanism can influence the other suggesting a combinatorial regulation, as evidenced by the methylation of histones being implicated in the modulation of DNA methylation.

Covalent histone modifications, a key mechanism involved in epigenetic control, include: (1) lysine acetylation, (2) lysine and arginine methylation, (3) serine and threonine phosphorylation, (4) ADP-ribosylation, (5) ubiquitination, and (6) SUMOylation. Specific enzymatic activities are associated with these modifications and in the case of histone methylation, methyltransferases catalyze the transfer of a methyl group from cofactor S-adenosylmethionine to a lysine or arginine, producing S-adenosylhomocysteine as a by-product. Methyltransferases can also modify residues in other cellular proteins, e.g. the tumor suppressor p53.

Histone methyltransferases fall into subgroups that include arginine methyltransferases, SET-domain containing methyltransferases SU(VAR)3-9, E(Z) and TRX, and DOT-like methyltransferase hDOT1L. Families of SET-domain containing methyltransferases have been identified and include SUV39, SET1, SET2 and RIZ.

The disruption of the normal functions of methyltransferases has been implicated in human diseases. Members of different classes of methyltransferases are implicated in cancer and representative examples for the subgroups and subclasses are provided: (1) hDOT1L, a member of the DOT-like methyltransferases, is linked to leukemogenesis [Nature Cell Biology, 8:1017-1028 (2006); Cell, 121:167-178 (2005); Cell, 112:771-723 (2003)]. (2) EZH2, a SET1 methyltransferase, is up-regulated in tumor cell lines and has been linked to breast, gastric and prostate cancers [British Journal of Cancer, 90:761-769 (2004)]. (3) SUV39-1/2, SUV39 methyltransferases, have been linked to signaling pathways regulating cancer cell growth and differentiation [Genetica, 117(2-3):149-58 (2003)]. (4) NSD1, a SET2 subclass methyltransferase, has been linked to acute myeloid leukemia and Sotos syndrome, a predisposition to cancer [Molecular Cell Biology, 24(12):5184-96 (2004)]. (5) EVI1, a RIZ methyltransferase, is overexpressed in solid tumors and leukemia [Proceeding of the National Academy of Sciences, 93:1642-1647 (1996)]. (6) Related enzymes, namely SMYD2, are lysine methyltransferases that modify the tumor suppressor protein, p53 and through this activity, may function as an oncogene that interferes with p53's protective functions [Nature, 444(7119):629-632 (2006)]. (7) SMYD3, a SET-domain containing lysine methyltransferase, is involved in cancer cell proliferation [Nature Cell Biology, 6(8):731-740 (2004)]. (8) CARM1, an arginine methyltransferase, is linked to prostate cancer [Prostate, 66(12):1292-301 (2006)].

Inappropriate methyltransferase activities thus represent attractive targets for therapeutic intervention by small molecule inhibitors. In fact, inhibitors of SUV(AR) histone methyltransferase [Nature Chemical Biology, 1:143-145 (2005)] and protein arginine methyltransferase [Journal of Biological Chemistry, 279:23892-23899 (2004)] have been described. The present invention relates to novel synthetic compounds effective as inhibitors of inappropriate histone methyltransferase activities that would be useful in treating human diseases, such as cancer.

SUMMARY OF THE INVENTION

In one aspect, the invention relates to compounds of general formulae I and II, which are potent and selective inhibitors of lysine and arginine methyltransferases:

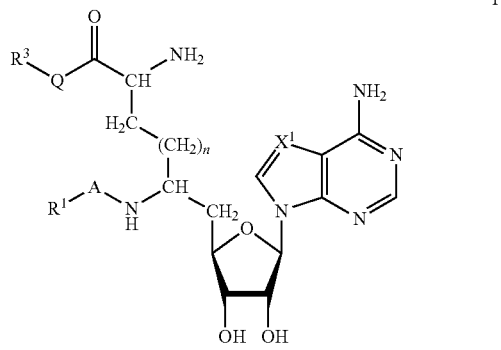

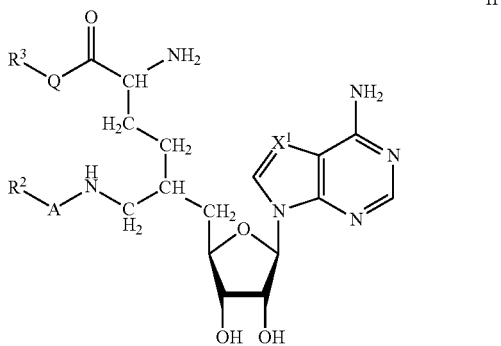

wherein:
X$^1$ is N or CH;
Q is NH or O;

A is chosen from direct bond, $(C_1-C_{20})$hydrocarbon, $(C_1-C_{20})$oxaalkyl and $(C_1-C_{20})$azaalkyl;

$R^1$ is chosen from hydrogen, —C(=NH)NH$_2$, —C(=NH)NH(C$_1$-C$_{10}$)hydrocarbon, fluoro(C$_1$-C$_6$)hydrocarbon, and —CH(NH$_2$)COOH, with the provisos that, (1) when A is a direct bond, $R^1$ cannot be H;

(2) when QR$^3$ is OH, $R^1$ cannot be fluoro(C$_2$-C$_6$)hydrocarbon;

$R^2$ is chosen from hydrogen, —C(=NH)NH$_2$, —C(=NH)NH(C$_1$-C$_{10}$)hydrocarbon and —CH(NH$_2$)COOH;

$R^3$ is chosen from H and $(C_1-C_{20})$ hydrocarbon; and n is 1 or 2.

In these compounds, A is a bivalent moiety and $R^1$ or $R^2$ is a substituent on A. The members of these genera are effective as inhibitors of methyltransferase activities and therefore, are useful for the inhibition, prevention and suppression of various pathologies associated with such activities, such as, for example, cancer cell and cancer stem cell fate differentiation, and cancer cell proliferation and cell cycle regulation. The compounds are also useful research tools for studying protein methyl transferase biology.

In another aspect, the invention relates to pharmaceutical compositions comprising a therapeutically effective amount of at least one compound of general formula I or II and a pharmaceutically acceptable carrier.

In another aspect, the invention relates to a method for treating cancer comprising administering to a subject suffering from a cancer a therapeutically effective amount of a compound of formula I or II.

DETAILED DESCRIPTION OF THE INVENTION

Throughout this specification the substituents are defined when introduced and retain their definitions.

In one aspect, the invention relates to compounds having general formula I:

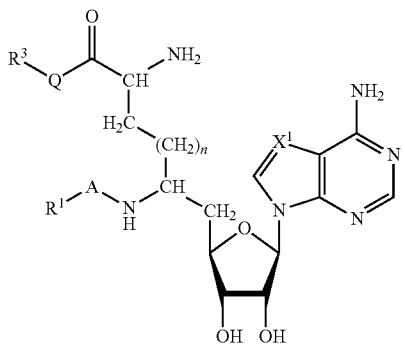

In some embodiments of I, $R^3$ is chosen from H, methyl and ethyl. In some embodiments n is 2. In some embodiments QR$^3$ is OH. In some embodiments n is 1 and QR$^3$ is OH; these fall into a genus of formula Ia:

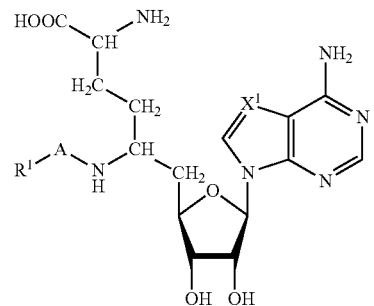

In some embodiments, $R^1$-A is chosen from $(C_1-C_6)$alkyl, benzyl and $(C_3-C_6)$oxaalkyl. In these embodiments, $R^1$ is conceptually H and A is, for example, —(CH$_2$CH$_2$CH$_2$)—; or $R^1$ is conceptually H and A is

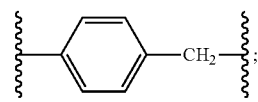 [SMILES: *Cc1ccc(*)cc1]

or $R^1$ is H and A is —(CH$_2$OCH$_2$CH$_2$CH$_2$)—. In other embodiments, $R^1$-A is chosen from amino(C$_1$-C$_6$)alkyl, benzylamino(C$_1$-C$_6$)alkyl and guanidino(C$_1$-C$_6$)alkyl. In this latter compound, $R^1$ is —C(=NH)NH$_2$ and A is considered an azaalkyl, for example, —NHCH$_2$CH$_2$—.

In some embodiments $R^1$-A may be chosen from HOOC(NH$_2$)CH-azaalkyl and NH$_2$(NH=)C-azaalkyl.

In another aspect the invention relates to compounds having general formula II

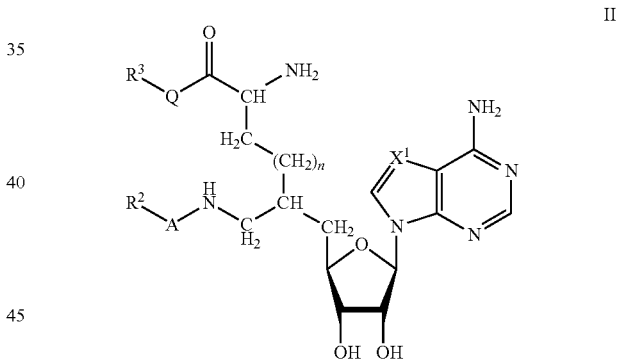

In some embodiments of II, $R^3$ is chosen from H, methyl and ethyl. In some embodiments n is 2. In some embodiments QR$^3$ is OH. In some embodiments n is 1 and QR$^3$ is OH; these fall into a genus of formula IIa:

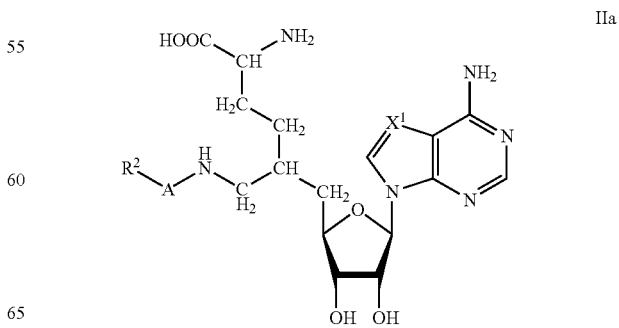

In some embodiments R²-A is chosen from hydrogen, (C₁-C₆)alkyl, benzyl and —C(=NH)NH₂.

When A is azaalkyl, the number of carbons between nitrogens is preferably two or three. Thus, R¹-A and R²-A may be, for example, aminoethyl, benzylaminoethyl, guanidinoethyl, and (C₁-C₆)alkyaminoethyl.

In all of the foregoing embodiments, X¹ may be CH, i.e. the heterocycle is 7-deazapurine (also known as 7H-pyrrolo[2,3-d]pyrimidine) or X¹ may be N, i.e. the heterocycle is purine.

For convenience and clarity certain terms employed in the specification, examples and claims are described herein.

Unless otherwise specified, alkyl (or alkylene) is intended to include linear, branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of C₁₀ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

C₁ to C₂₀ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus (C₃-C₁₀) carbocycle refers to both non-aromatic and aromatic systems, including such systems as cyclopropane, benzene and cyclohexene; (C₈-C₁₂) carbopolycycle refers to such systems as norbornane, decalin, indane and naphthalene. Carbocycle, if not otherwise limited, refers to monocycles, bicycles and polycycles.

Alkoxy or alkoxyl refers to groups of from 1 to 8 carbon atoms of a straight, branched or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purpose of this application, alkoxy and lower alkoxy include methylenedioxy and ethylenedioxy.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples of azaalkyl include ethylaminoethyl and aminohexyl.

Substituents R" are generally defined when introduced and retain that definition throughout the specification and in all independent claims.

As used herein, and as would be understood by the person of skill in the art, the recitation of "a compound"—unless expressly further limited—is intended to include salts of that compound. Thus, for example, the recitation "a compound of formula I" as depicted above, which depicts a substituent COOH, would include salts in which the substituent is COO⁻ M⁺, wherein M is any counterion. Similarly, formula I as depicted above depicts a substituent NH₂, and therefore would also include salts in which the substituent is NH₃⁺ X⁻, wherein X is any counterion. The compounds may commonly exist as zwitterions, which are effectively internal salts. In a particular embodiment, the term "compound of formula I" refers to the compound or a pharmaceutically acceptable salt thereof. As used herein, and as would be understood by the person of skill in the art, the recitation of "a compound"—unless expressly further limited—is intended to include salts of that compound. In a particular embodiment, the term "compound of formula I" refers to the compound or a pharmaceutically acceptable salt thereof.

The term "pharmaceutically acceptable salt" refers to salts whose counter ion derives from pharmaceutically acceptable non-toxic acids and bases. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include ²H, ³H, ¹¹C, ¹³C, ¹⁴C, ¹⁵N, ³⁵S, ¹⁸F, ³⁶Cl, ¹²⁵I, ¹²⁴I and ¹³¹I respectively. Compounds that contain those radioisotopes and/or other radioisotopes of other atoms are within the scope of this invention. Tritiated, i.e. ³H, and carbon-14, i.e., ¹⁴C, radioisotopes are particularly preferred for their ease in preparation and detectability. Compounds that contain isotopes ¹¹C, ¹³N, ¹⁵O, ¹²⁴I and ¹⁸F are well suited for positron emission tomography. Radiolabeled compounds of formulae I and II of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genera I and II that are not already in the possession of the public.

While it may be possible for the compounds of formula I or II to be administered as the raw chemical, it is preferable to present them as a pharmaceutical composition. According to a further aspect, the present invention provides a pharmaceutical composition comprising a compound of formula I or II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, subcutaneously, and directly into the CNS—either intrathecally or intracerebroventricularly.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological systems of a disease, even though a diagnosis of this disease may not have been made.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials are either commercially available, synthesized as described in the examples or may be obtained by the methods well known to persons of skill in the art.

Scheme 1

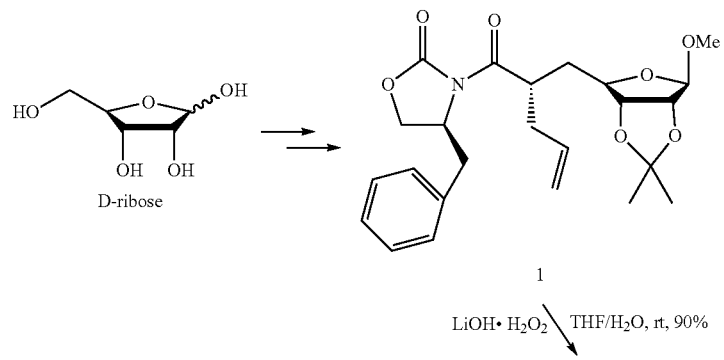

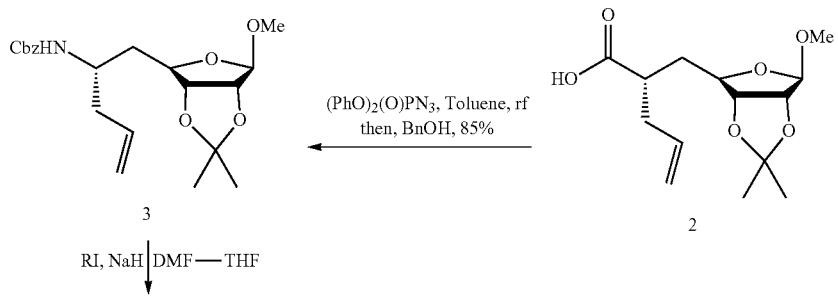
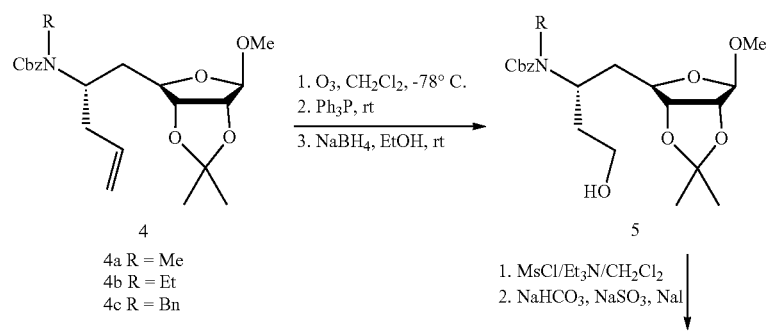
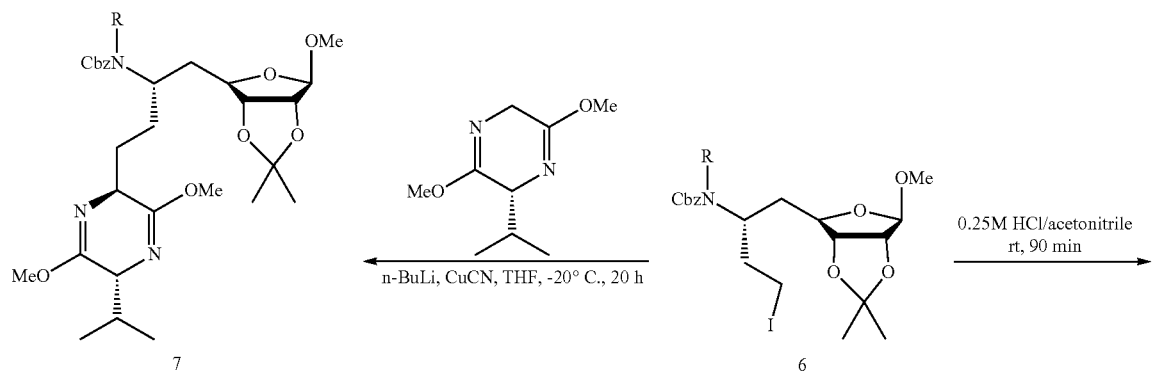
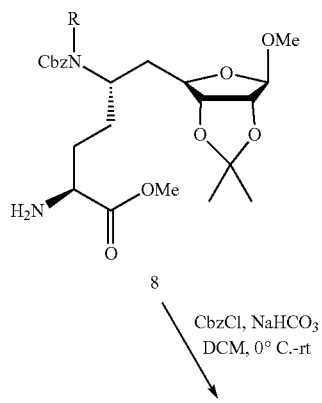

-continued
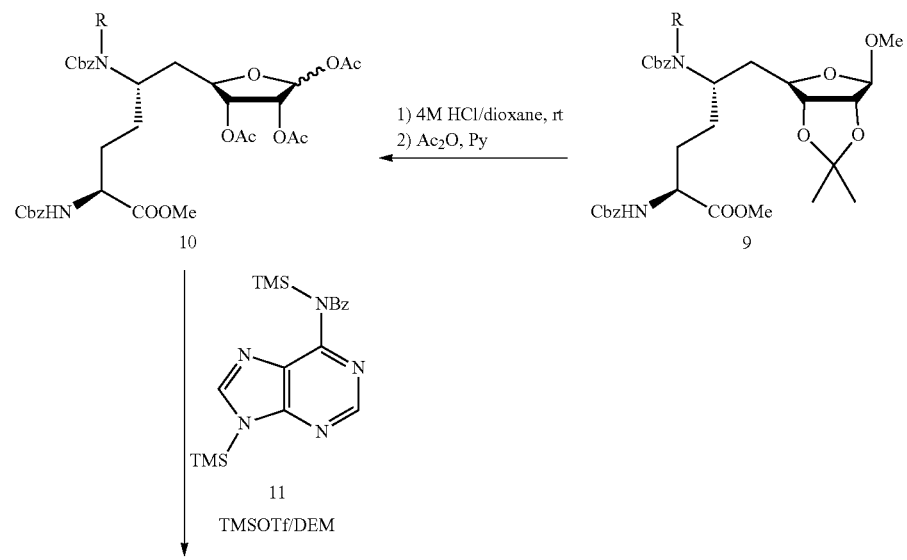
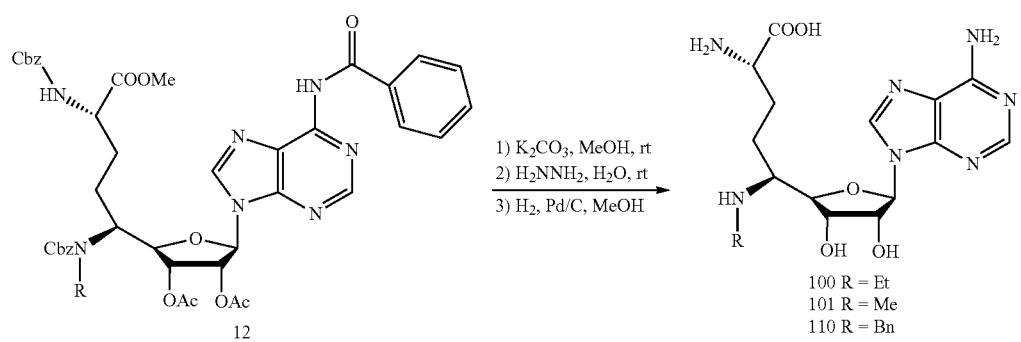
Scheme 2
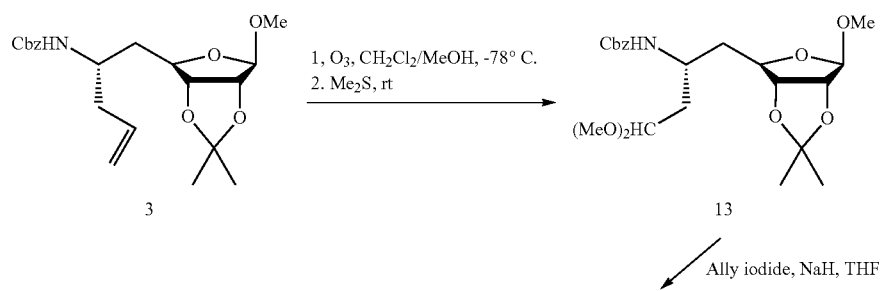

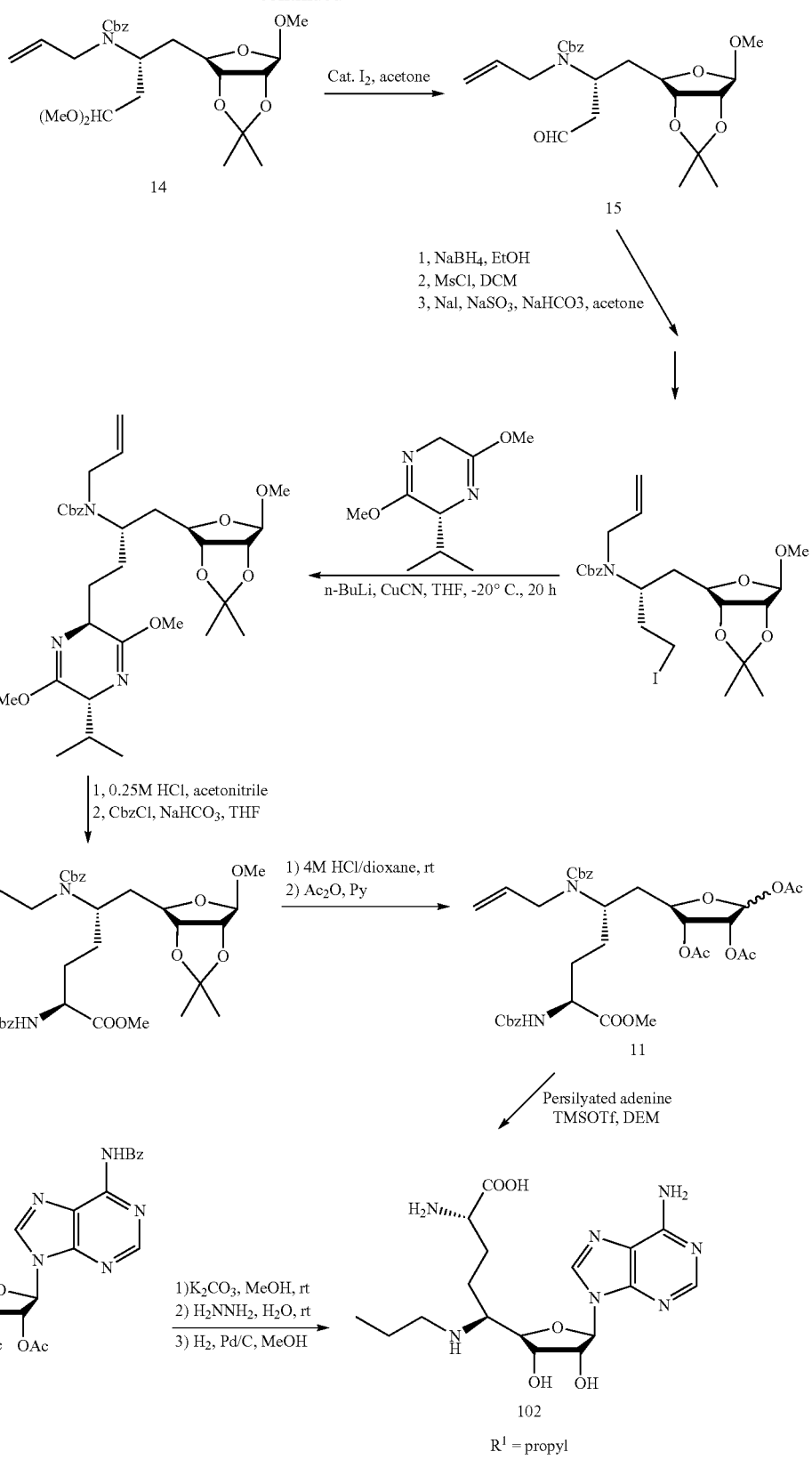

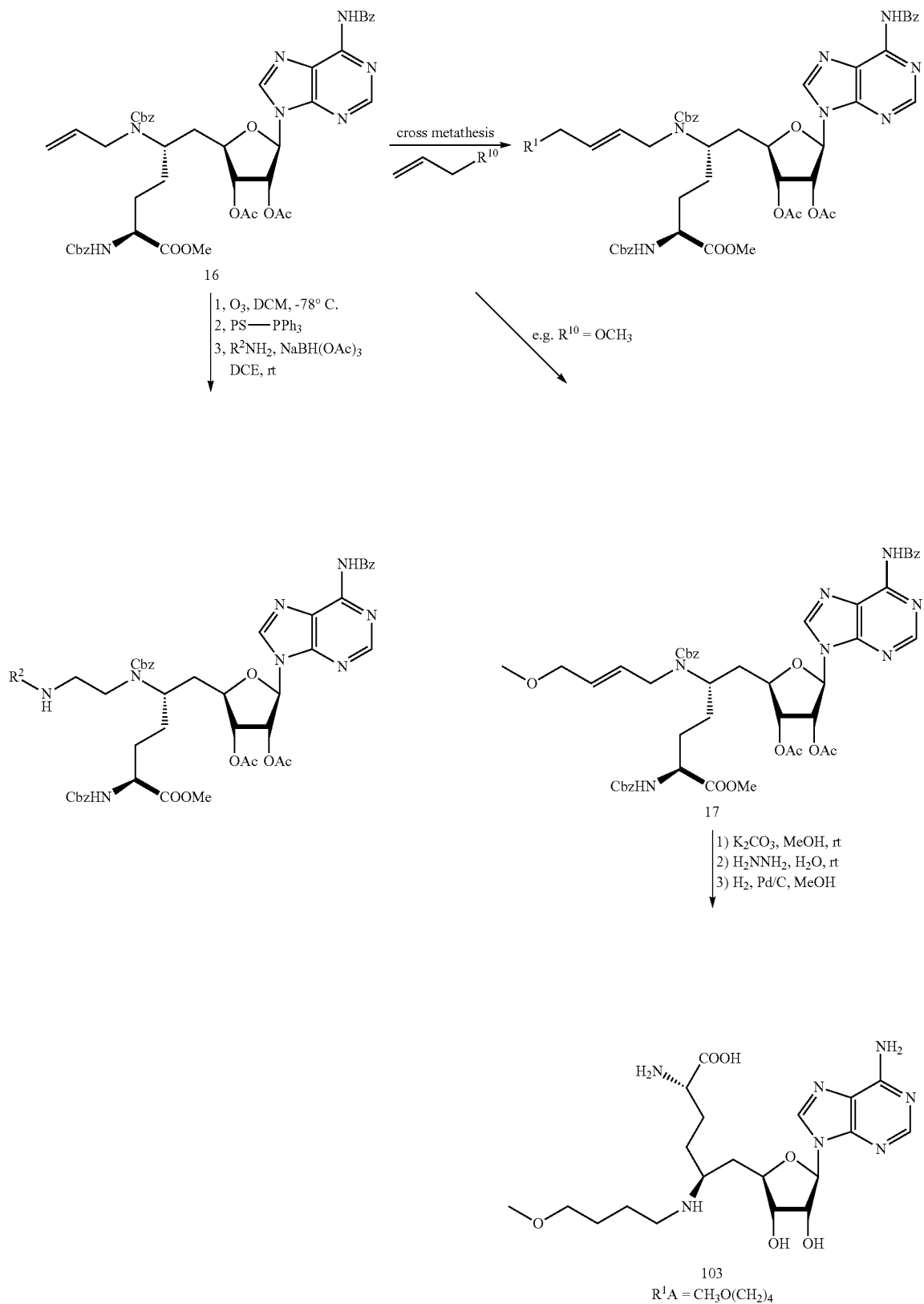

Scheme 4
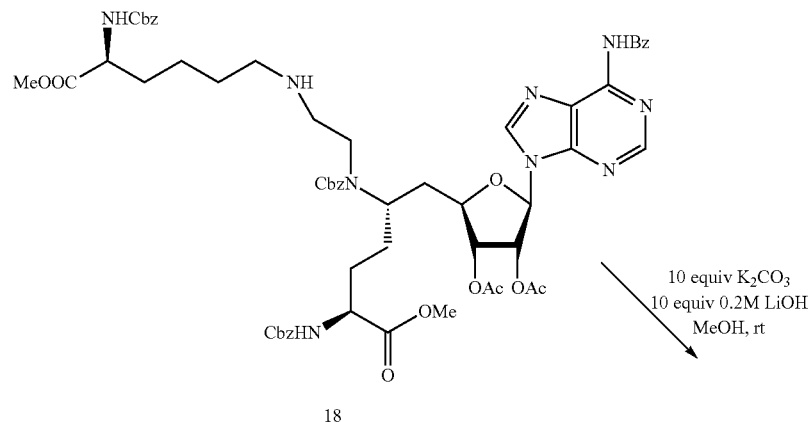
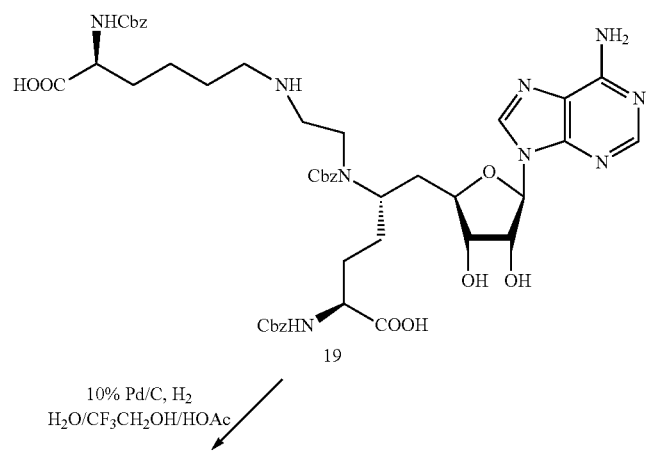
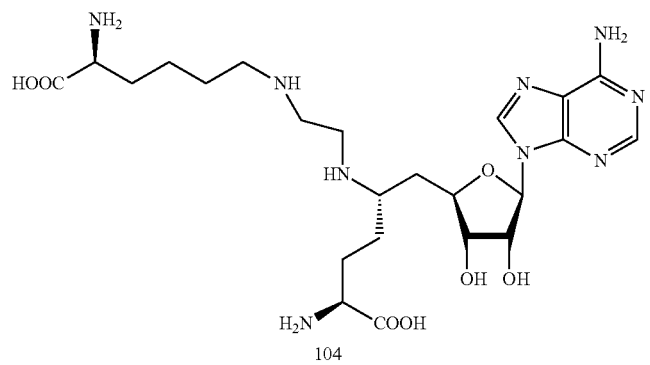

Scheme 5
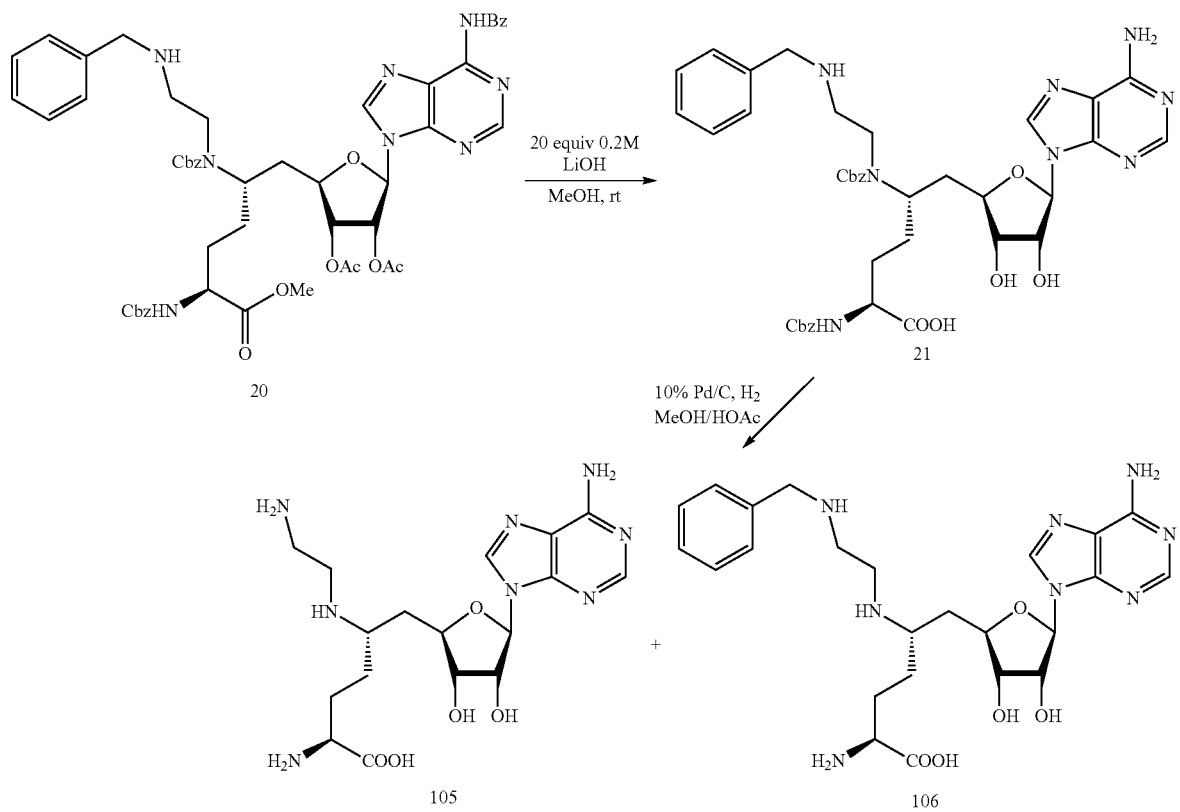
Scheme 6
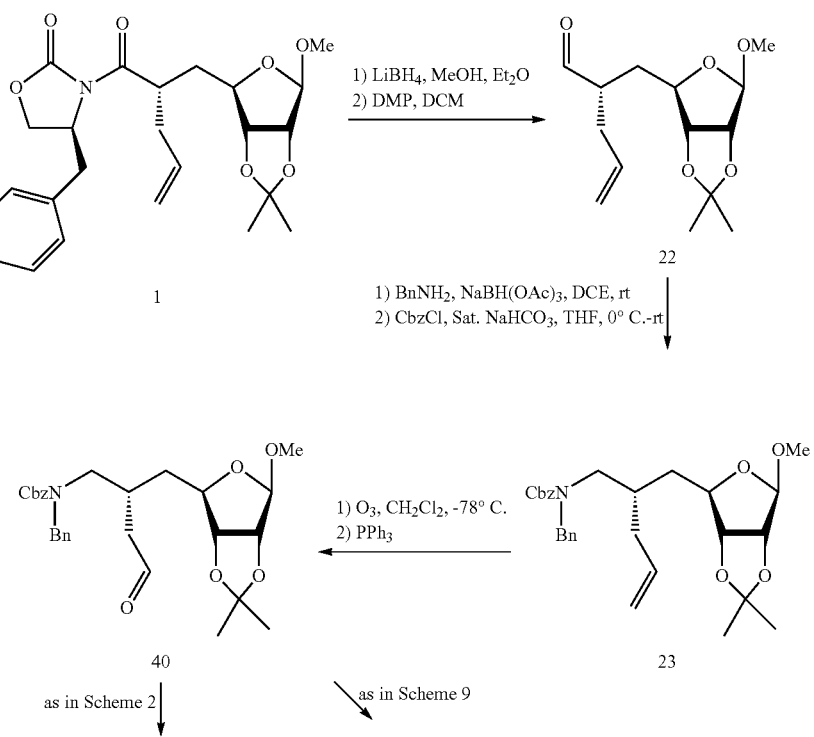

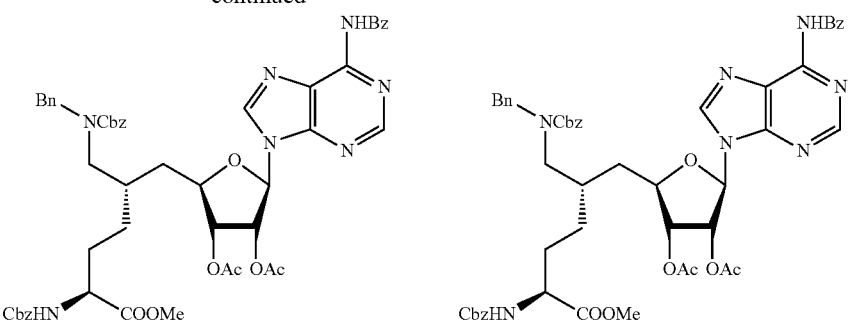
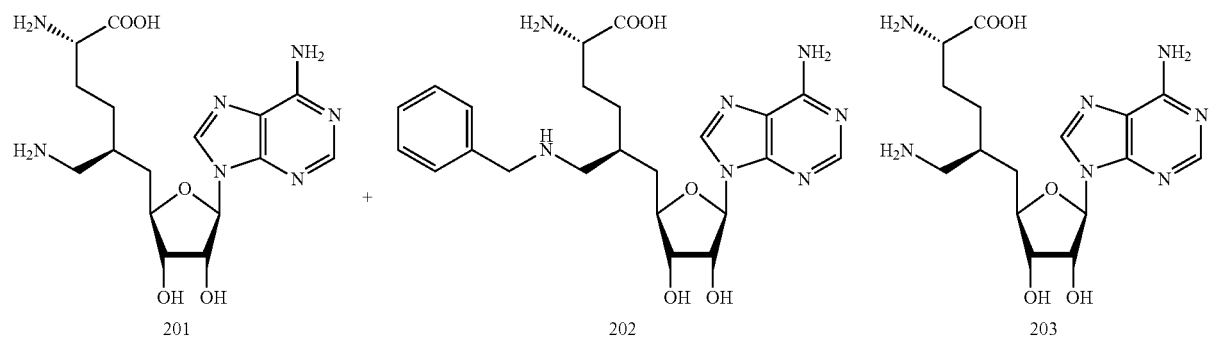
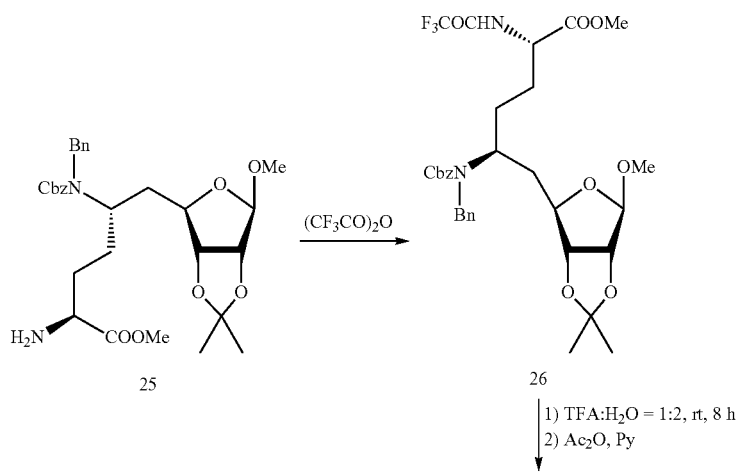

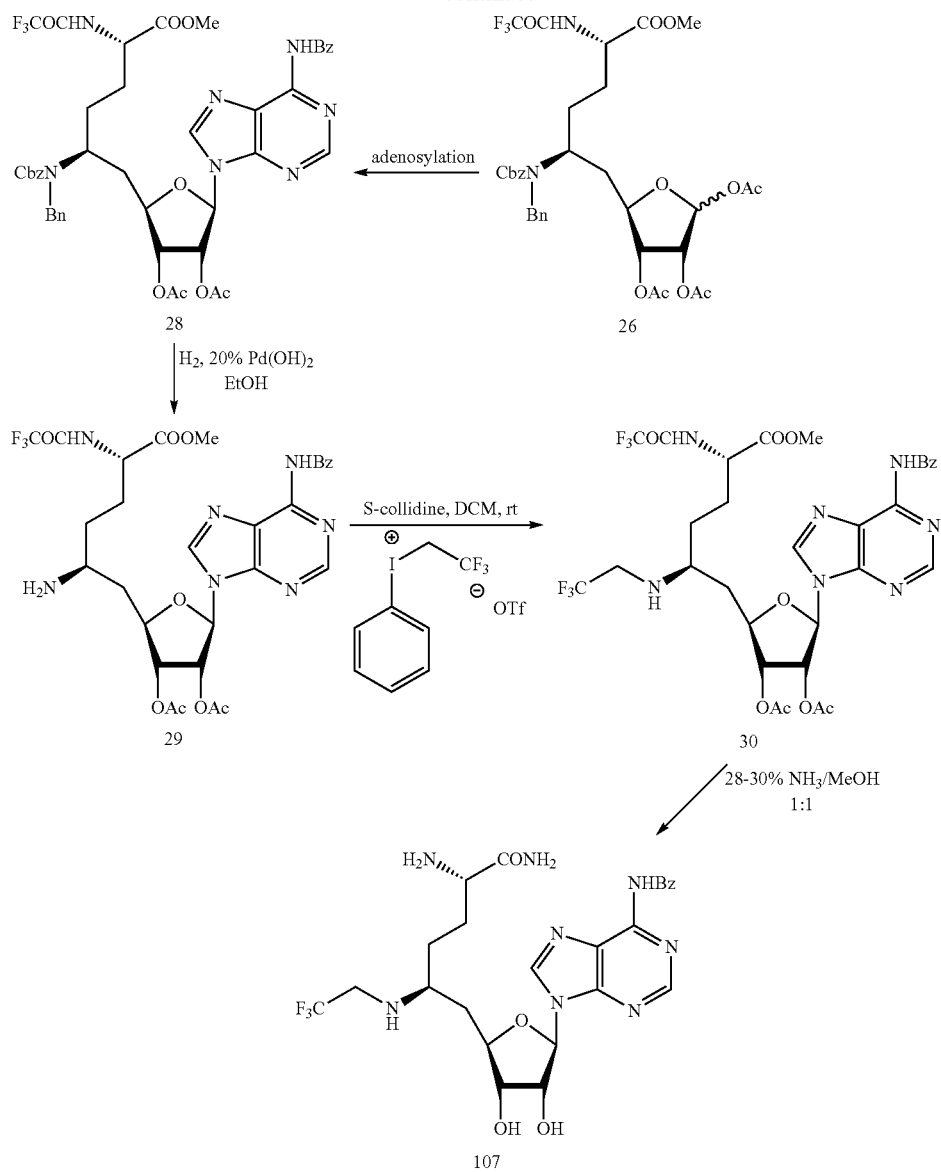
-continued
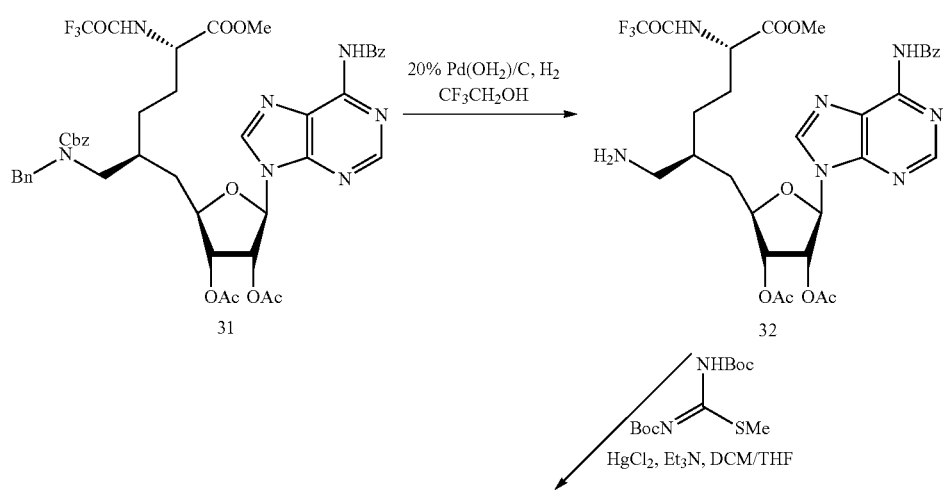
Scheme 8

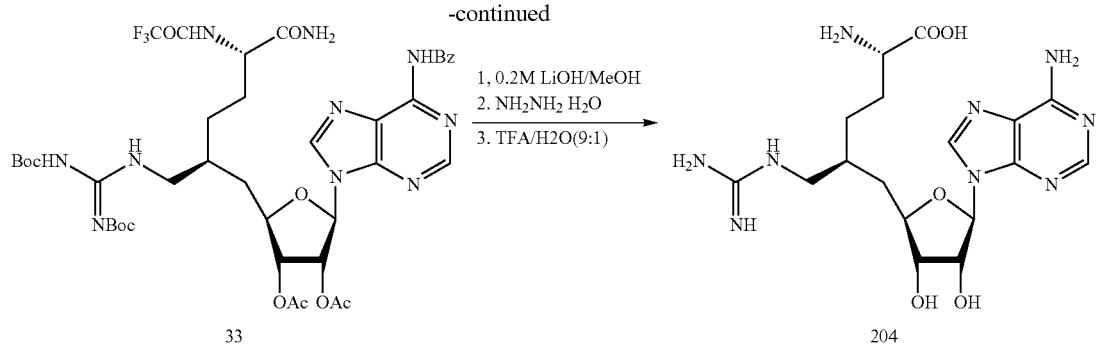
In analagous fashion to that shown in Scheme 7, compound 205 was synthesized from intermediate 32:
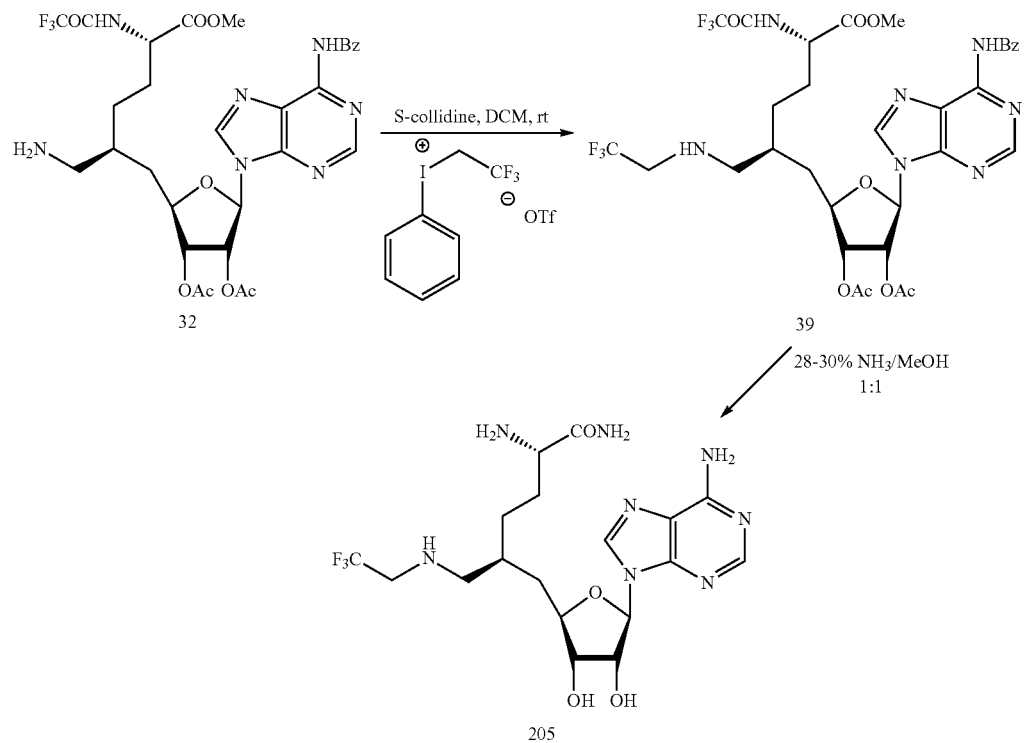
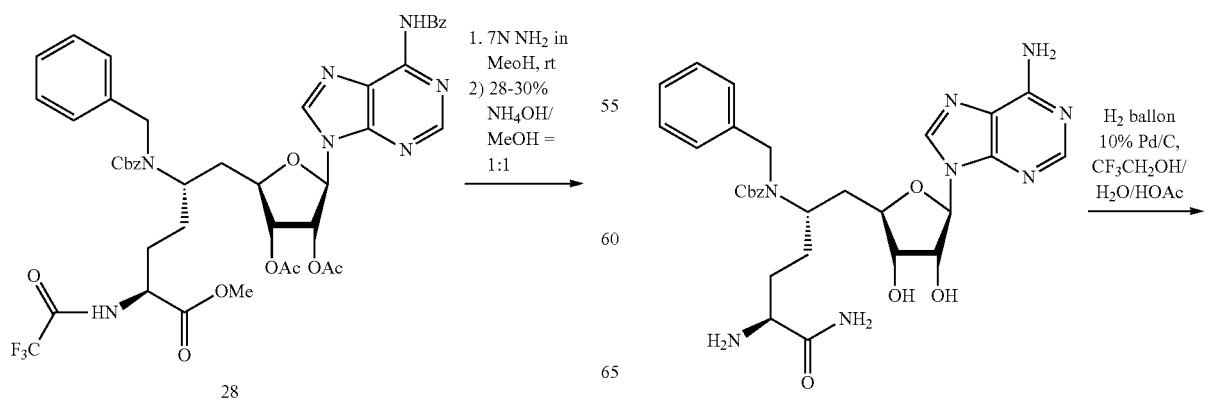

27
-continued
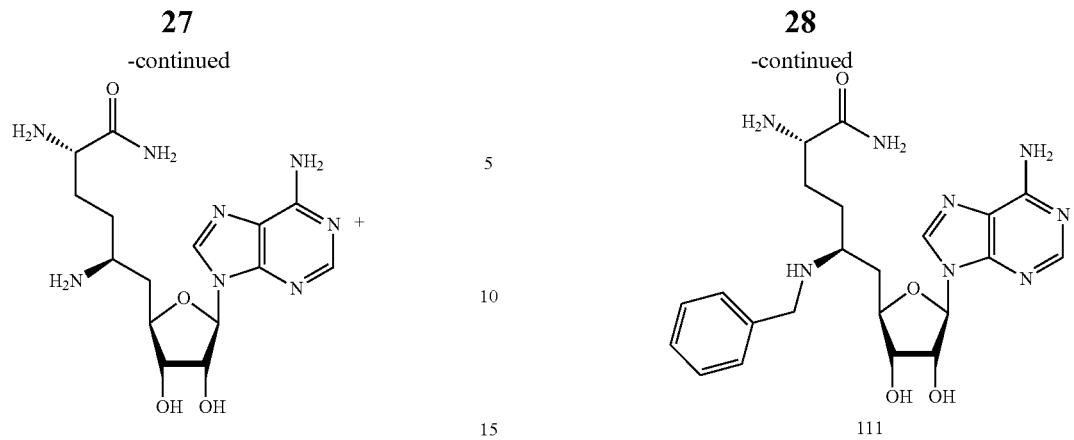
28
-continued
Scheme 11
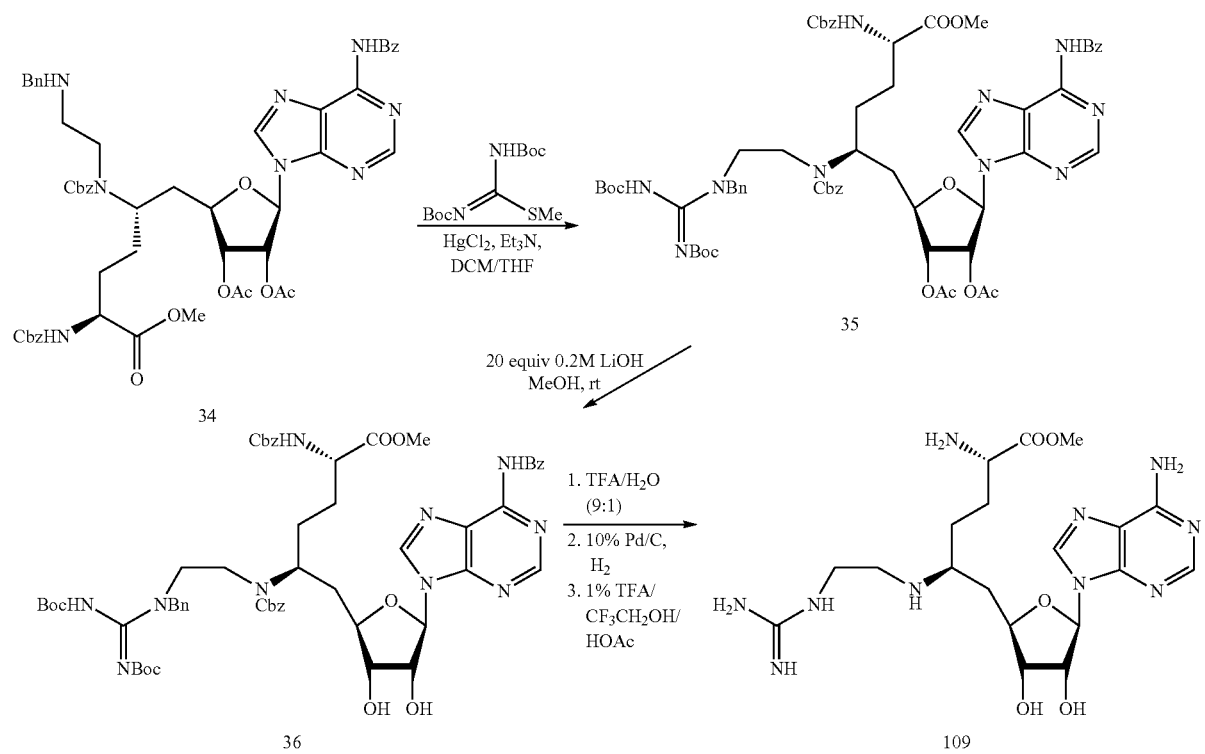
Deazapurines were synthesized as shown in Scheme 12:
Scheme 12
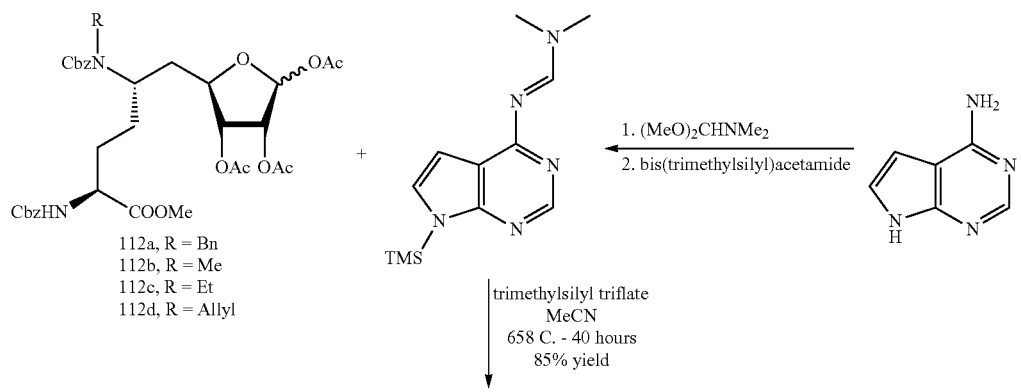

-continued

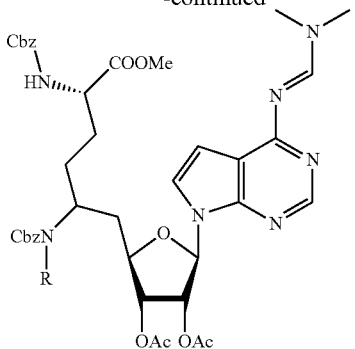

115a, R = Bn
115b, R = Me
115c, R = Et
115d, R = Allyl 1. 0.2M, LiOH
   methanol
   r.t.
2. H₂
   10% Pd/C
   EtOH/H₂O/HOAc

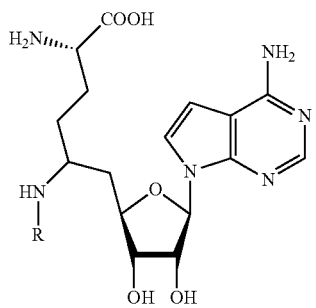

116a, R = H
116b, R = Me
116c, R = Et
116d, R = Pr

In the deprotection Step 1. for 115d, a by-product was isolated in which the acetates were cleaved but the methyl ester was not. These were separated, and in a subsequent Step 2, the CBZ was cleaved and the allyl group was reduced to provide, in addition to the fully deprotected and reduced products 116a-116d, the methyl ester of the acid 116d, which is identified as 116e:

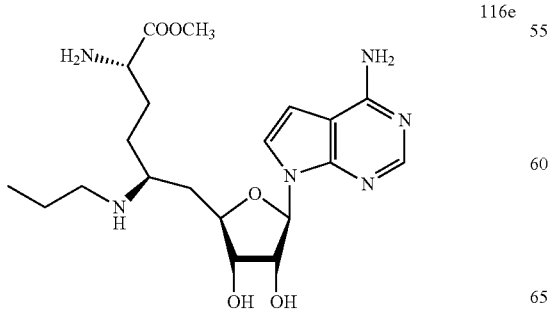

116e

Compounds in which n is 2 are synthesized as described in Scheme 13:

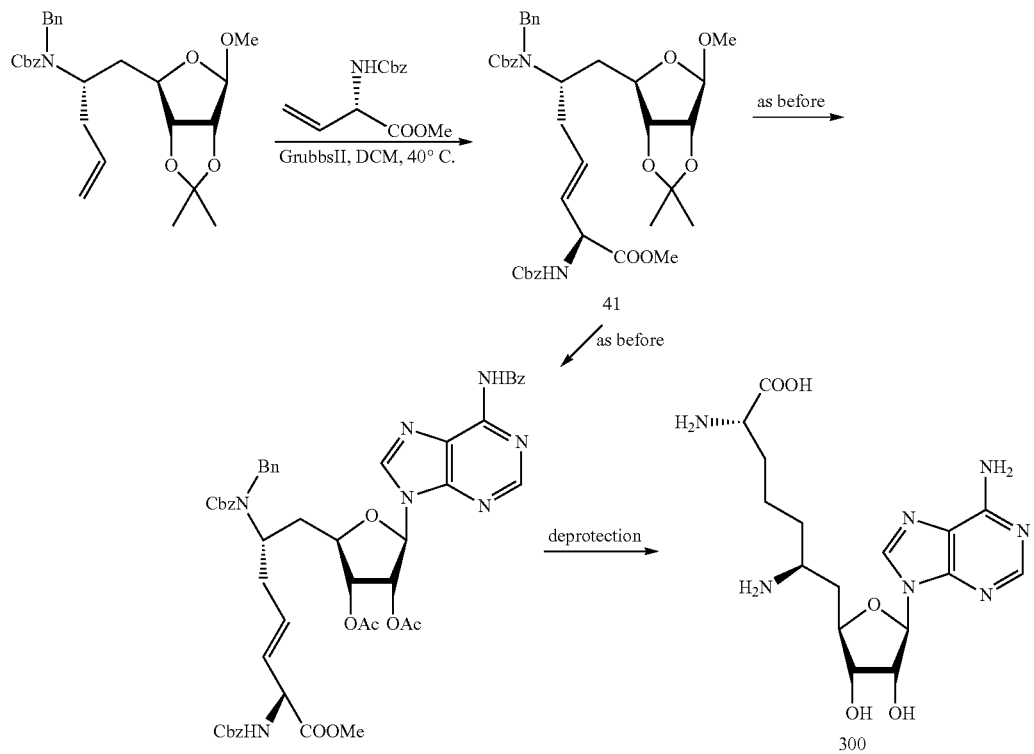

Scheme 13

Synthesis of 4a, 4b, 4c. To a stirred suspension of sodium hydride (60%, 86 mg, 2.1 mmol) in 5 mL THF at ambient temperature was added dropwise the solution of the urethane 3 (160 mg, 0.36 mmol) in 20 mL THF. After the mixture was stirred for 1 h, the corresponding halides (2.1 mmol) were added (methyl/ethyl/allyl iodide or benzyl bromide), followed by tetrabutylammonium iodide (10 mg). The resultant mixture was stirred for 20 h. The reaction was then quenched with saturated aqueous NH$_4$Cl (20 mL) and volatile components in the mixture was removed under reduced pressure. This mixture was further extracted with ethyl acetate (3×30 mL). The combined organic phase was washed with brine and then dried with anhydrous Na$_2$SO$_4$. After removing volatile components, the crude mixture was purified by silica gel chromatography (hexane:EtOAc=3:1 then 2:1) to yield Compounds 4a, 4b, 4c as colorless oil.

4a R=Me, 85% yield. $[\alpha]_D^{18.9}$+7.83 (c 1.30, CHCl$_3$); $^1$H-NMR (600 MHz, DMSO-d$_6$, 74° C.): δ 1.25 (s, 3H), 1.38 (s, 3H), 1.60-1.64 (m, 1H), 1.78-1.82 (m, 1H), 2.17-2.21 (m, 1H), 2.30-2.31 (m, 1H), 2.75 (s, 1H), 3.27 (s, 3H), 3.96 (dd, 1H, J=10.4 Hz, 4.2 Hz), 4.22-4.23 (m, 1H), 4.54 (d, 1H, J=5.9 Hz), 4.56 (d, 1H, J=5.9 Hz), 4.85 (s, 1H), 4.99 (dt, 1H, J=10.2 Hz, 0.9 Hz), 5.05 (d, 1H, J=10.2 Hz), 5.09 (d, 2H, J=1.2 Hz) 5.63-5.72 (m, 1H), 7.28-7.31 (m, 1H), 7.33-7.36 (m, 4H); $^{13}$C-NMR (125 MHz, CDCl$_3$, rotamers): δ 24.61, 24.96, 26.41, 26.47, 36.77, 37.23, 37.35, 37.64, 55.15, 55.30, 66.89, 67.24, 83.75, 83.82, 84.38, 84.48, 85.55, 85.60, 109.86, 110.00, 112.26, 112.35, 117.24, 117.40, 127.65, 127.80, 127.87, 128.31, 128.41, 134.57, 134.89, 136.92, 137.07, 165.42, 165.74; MS (ESI) m/z: 428 [M+Na]$^+$; HRMS: calculated for C$_{22}$H$_{31}$NO$_6$Na ([M+Na]$^+$) 428.2049. found 428.2036.

4b R=Et, 57% yield. $[\alpha]_D^{18.9}$+3.38 (c 0.87, CHCl$_3$); $^1$H-NMR (600 MHz, DMSO-d$_6$, 74° C.): δ 1.11 (t, 3H, J=7.0 Hz), 1.26 (s, 3H), 1.38 (s, 3H), 1.63-1.67 (m, 1H), 1.89-1.91 (m, 1H), 2.23-2.27 (m, 1H), 2.35-2.40 (m, 1H), 3.18-3.23 (m, 2H), 3.27 (s, 3H), 3.96-3.98 (m, 1H), 4.01 (dd, 1H, J=10.7 Hz, 3.6 Hz), 4.54 (d, 1H, J=6.2 Hz), 4.55 (d, 1H, J=5.9 Hz), 4.85 (s, 1H), 4.99 (dt, 1H, J=10.2 Hz, 1.0 Hz), 5.05 (dd, 1H, J=10.2 Hz, 1.7 Hz), 5.10 (s, 2H), 5.68-5.75 (m, 1H), 7.29-7.31 (m, 1H), 7.34-7.35 (m, 4H); $^{13}$C-NMR (150 MHz, DMSO-d$_6$ rotamers): δ 14.35, 15.22, 24.64, 26.25, 36.50, 37.05, 37.59, 38.10, 54.49, 65.78, 66.08, 83.24, 83.32, 83.75, 84.81, 109.08, 109.21, 111.33, 117.08, 117.20, 127.25, 127.36, 127.70, 128.30, 128.40, 135.39, 135.58, 137.04, 137.25, 155.21, 155.39; MS (ESI) m/z: 442 [M+Na]$^+$, HRMS: calculated for C$_{23}$H$_{33}$NO$_6$Na ([M+Na]$^+$) 442.2206. found 442.2206.

4c R=Bn, 86% yield. $^1$H-NMR (600 MHz, DMSO-d$_6$, 74° C.): δ 1.23 (s, 3H), 1.36 (s, 3H), 1.61-1.66 (m, 1H), 1.86-1.89 (m, 1H), 2.22-2.26 (m, 1H), 2.28-2.31 (m, 1H), 3.22 (s, 3H), 3.94-3.96 (m, 2H), 4.33 (s, 1H), 4.36-4.38 (m, 2H), 4.48 (d, 1H, J=5.9 Hz), 4.54 (d, 1H, J=15.6 Hz), 4.83 (s, 1H), 4.90 (s, 1H), 4.92 (d, 1H, J=5.2 Hz), 5.14 (s, 2H), 5.53-5.60 (m, 1H), 7.23-7.24 (m, 1H), 7.29-7.34 (m, 9H); $^{13}$C-NMR (150 MHz, DMSO-d$_6$ rotamers): δ24.65, 26.23, 36.45, 37.12, 37.46, 38.05, 54.51, 66.18, 66.60, 83.08, 83.21, 83.56, 84.75, 109.08, 111.27, 117.09, 126.96, 127.44, 127.56, 127.74, 128.23, 128.29, 135.16, 135.33, 136.80, 138.89, 155.30, 156.51; MS (ESI) m/z: 504 [M+Na]$^+$.

Synthesis of 5. To a stirred CH$_2$Cl$_2$ solution containing the alkene 4 (0.29 mmol) was bubbled a stream of ozone at −78° C. until the blue color persisted over 5 min. After the solution was flushed with argon and turned transparent, triphenylphosphine (220 mg, 0.87 mmol) was added at −78°

C. The dry ice bath was then removed and the reaction mixture was allowed to warm up spontaneously at ambient temperature. The resultant reaction mixture was stirred until the ozonide intermediates disappeared (monitored by TLC, ~20 h). Evaporation of the solvent under reduced pressure gave the crude aldehyde, which was purified by flash silica gel chromatography (hexane:EtOAc=2:1 then 1:1) to yield the product as colorless oil. Without further storage, the intermediated aldehyde (around 0.22 mmol) was dissolved in 15 mL ethanol and reacted with NaBH$_4$ (10 mg, 0.29 mmol, added by batch) at 0° C. under argon. The reaction mixture was stirred at 0° C. for 20 min and then quenched with saturated aqueous NH$_4$Cl solution (20 mL, added dropwise). The resultant mixture was diluted with 20 mL ethyl acetate. The organic phase was separated and the aqueous phase was further extracted with ethyl acetate (3×30 mL). The combined organic phase was washed with brine, dried with Na$_2$SO$_4$ and concentrated. The crude mixture was purified by a short column chromatography (hexane:EtOAc=1:1 then 1:2) to give the corresponding alcohols 5a, 5b and 5c.

5b R=Et, 95% yield. $[\alpha]_D^{17.9}$+1.38 (c 1.17, CHCl$_3$); $^1$H-NMR (600 MHz, DMSO-d$_6$ 74° C.): δ 1.11 (t, 3H, J=7.0 Hz), 1.26 (s, 3H), 1.38 (s, 3H), 1.59-1.66 (m, 2H), 1.80-1.83 (m, 1H), 1.91-1.93 (m, 1H), 3.20-3.27 (m, 2H), 3.38 (s, 3H), 3.40 (q, 2H, J=6.0 Hz), 3.97 (br, 1H), 4.01 (dd, 1H, J=10.6 Hz, 3.7 Hz), 4.10-4.11 (m, 1H), 4.53 (d, 1H, J=6.0 Hz), 4.55 (d, 1H, J=6.0 Hz), 4.86 (s, 1H), 5.09 (s, 2H), 7.29-7.31 (m, 1H), 7.34-7.36 (m, 4H); $^{13}$C-NMR (150 MHz, DMSO-d$_6$ rotamers): δ4.92, 24.66, 26.25, 37.11, 37.75, 54.41, 57.79, 57.86, 65.69, 66.02, 83.43, 83.75, 84.81, 109.04, 109.14, 111.30, 127.23, 127.68, 128.26, 128.40, 137.27, 155.45; MS (ESI) m/z: 446 [M+Na]$^+$; HRMS: calculated for C$_{22}$H$_{33}$NO$_7$Na ([M+Na]$^+$) 446.2155. found 446.2148.

Synthesis of 6. To the solution of the primary alcohol 5 (0.4 mmol) in 20 mL dry dichloromethane (DCM) was added triethyl amine (82 μL, 0.59 mmol) and then methanesulfonyl chloride (39 μL, 0.5 mmol) at 0° C. The resultant mixture was stirred at 0° C. for additional 30 min, diluted with another 20 mL DCM, washed with 30 mL saturated aqueous NaHCO$_3$ solution. The organic layer was separated. The aqueous phase was further extracted with DCM (3×20 mL). The combined organic phase was washed with brine and dried with anhydrous Na$_2$SO$_4$. After removing volatile components and without any purification, the crude methanesulfonate was redissolved with 25 mL acetone. To the resultant reaction mixture was added sodium bicarbonate (160 mg, 1.95 mmol), sodium sulfite (147 mg, 1.17 mmol) and sodium iodide (580 mg, 3.9 mmol). The suspension was heated to 50° C. and stirred for about 3 hr under argon. Upon the completion of the reaction, 20 mL water was added and the resultant mixture was concentrated under reduced pressure. The residual mixture was then extracted with ethyl acetate (3×30 mL). The combined organic phase was washed with brine and dried with anhydrous Na$_2$SO$_4$. Removal of the volatile components, followed by purification with silica gel chromatography (hexane:EtOAc=4:1 then 3:1) yield the final product 6.

6 b R=Et, 70% yield. $[\alpha]_D^{17.9}$−10.9 (c 0.91, CHCl$_3$); $^1$H-NMR (600 MHz, CDCl$_3$, rotamers): δ 1.18-1.23 (m, 3H), 1.30 (s, 3H), 1.47 (s, 3H), 1.59-1.63 (m, 1H), 1.92-1.94 (m, 0.4H), 2.00-2.04 (m, 0.6H), 2.17 (br, 0.4H), 2.43 (br, 0.6H), 3.02-3.03 (m, 0.4H), 3.09-3.13 (m, 1H), 3.15-3.17 (m, 0.6H), 3.23-3.30 (m, 3H), 3.42 (s, 2H), 4.12-4.19 (m, 1H), 4.44 (d, 0.4H, J=5.8 Hz), 4.52 (d, 0.6H, J=5.8 Hz), 4.56 (d, 0.4H, J=5.8 Hz), 4.61 (d, 0.6H, J=5.8 Hz), 4.90 (s, 0.4H), 4.96 (s, 0.6H), 5.10-5.14 (m, 1.6H), 5.19 (d, 0.4H, J=12.2 Hz), 7.31-7.38 (m, 5H); $^{13}$C-NMR (150 MHz, CDCl$_3$, rotamers): δ 14.92, 15.47, 25.10, 25.17, 26.63, 26.66, 37.50, 37.78, 38.53, 38.62, 55.78, 55.98, 67.00, 67.47, 83.82, 83.98, 84.59, 84.68, 85.72, 85.76, 110.24, 110.44, 112.45, 112.59, 127.89, 128.13, 128.40, 128.65, 128.72, 136.75, 136.99, 155.72, 156.33. MS (ESI) m/z: 556 [M+Na]$^+$; HRMS: calculated for C$_{22}$H$_{32}$NO$_6$NaI ([M+Na]$^+$) 556.1172. found 556.1169.

Synthesis of 7. n-Butyllithum (500 μL, 1.6 M in hexane) was added dropwise to a stirred solution of (2R)-2,5-dihydro-2-isopropyl-3,6-dimethoxypyrazine (150 μL, 0.83 mmol) in 3 mL dry THF at −78° C. under argon atmosphere. The resultant mixture was allowed to be stirred for additional 5 min. The obtained yellow solution was subsequently transferred via a double-tipped needle to stirred slurry of copper (I) cyanide (38 mg, 0.42 mmol) in 2 mL THF at −78° C. under argon. This mixture was stirred at 0° C. for around 1.5 min to afford cyanocuprate as a tan colored solution. The reaction was then immediately cooled down to −78° C. A solution of the iodide 6 (0.28 mmol) in 10 mL dry THF was then added dropwise. The reaction mixture was stirred at −78° C. for 30 min and then for 16 h at −25° C. under argon. The reaction was quenched by adding a 1:9 mixture of aqueous ammonia/saturated aqueous ammonium chloride (15 mL). The aqueous phase was further extracted with diethyl ether (3×20 mL). The organic layer was combined and then washed with the 1:9 mixtures of concentrated aqueous ammonia/saturated aqueous ammonium chloride, followed by brine, and then dried with anhydrous Na$_2$SO$_4$. After removing the volatile components with rotavapor, the crude product was purified by silica gel flash chromatography (hexane:EtOAc=4:1 then 3:1) afforded the desired product 7 as colorless oil.

7b R=Et, 79% yield. $[\alpha]_D^{17.9}$+6.75 (c 1.01, CHCl$_3$); $^1$H-NMR (600 MHz, DMSO-d$_6$, 64° C.): δ 0.65 (d, 3H, J=6.8 Hz), 0.99 (d, 3H, J=6.8 Hz), 1.10 (t, 3H, J=7.0 Hz), 1.25 (s, 3H), 1.37 (s, 3H), 1.45-1.48 (m, 1H), 1.50-1.60 (m, 3H), 1.71-1.75 (m, 1H), 1.82-1.85 (m, 1H), 2.15-2.20 (m, 1H), 3.14-3.19 (m, 2H), 3.25 (s, 3H), 3.60 (s, 3H), 3.61 (s, 3H), 3.89 (t, 1H, J=3.6 Hz), 3.98 (dd, 1H, J=10.8 Hz, 4.0 Hz), 3.99-4.01 (m, 2H), 4.53 (d, 1H, J=5.9 Hz), 4.55 (d, 1H, J=5.9 Hz), 4.86 (s, 1H), 5.09 (s, 2H), 7.30-7.31 (m, 1H), 7.33-7.36 (m, 4H); $^{13}$C-NMR (150 MHz, DMSO-d$_6$ rotamers): δ 14.20, 15.17, 16.38, 19.01, 24.64, 26.23, 27.90, 30.73, 31.03, 37.52, 37.88, 52.07, 53.83, 54.03, 54.27, 59.77, 65.81, 66.13, 83.29, 83.41, 83.66, 83.70, 84.90, 109.05, 109.22, 111.32, 127.22, 127.60, 127.68, 128.21, 128.36, 136.97, 137.26, 155.52, 162.76, 163.03, 163.11; MS (ESI) m/z: 590 [M+H]$^+$; HRMS: calculated for C$_{31}$H$_{48}$N$_3$O$_8$ ([M+H]$^+$) 590.3441. found 590.3440.

Synthesis of 9. To a solution of the dihydropyrazine 7 (0.25 mmol) in 8 mL acetonitrile was added 6 mL 0.25 M aqueous HCl. This mixture was stirred for 2 hr at ambient temperature and then neutralized with 10 mL saturated aqueous NaHCO$_3$ solution at 0° C. The crude product was extracted with 20 mL ethyl acetate. The resultant aqueous phase was further extracted with ethyl acetate (3×20 mL). The combined organic layer was washed with brine, dried with anhydrous Na$_2$SO$_4$, and then concentrated under reduced pressure to give the corresponding crude α-amino methyl carboxylate 8. Without further purification, the α-amino methyl carboxylate was dissolved in 6 mL THF and cooled down to 0° C. Saturated aqueous NaHCO$_3$ solution of 0.4 mL was then added, followed by addition of 30 μL benzyl chloroformate. The resultant mixture was allowed to spontaneously warm up at ambient temperature and stirred for additional 8 hr. To the reaction mixture were added 20 mL ethyl acetate and 20 mL water. The organic layer was separated. The aqueous layer was further extracted with ethyl acetate (3×20 mL). The combined organic layer was washed with brine and dried with anhydrous $Na_2SO_4$. After removing volatile solvents, the crude reaction product was purified by silica gel flash chromatography on (hexane: EtOAc=3:1 then 3:2) to afford 9.

9b R=Et, 78% yield. $[\alpha]_D^{17.9}$+11.10 (c 1.21, $CHCl_3$); $^1$H-NMR (600 MHz, DMSO-$d_6$ at 64° C.): δ 1.10 (t, 3H, J=7.0 Hz), 1.25 (s, 3H), 1.38 (s, 3H), 1.54-1.68 (m, 5H), 1.83-1.85 (m, 1H), 3.10-3.15 (m, 1H), 3.16-3.21 (m, 1H), 3.24 (s, 3H), 3.62 (s, 3H), 3.98 (dd, 2H, J=10.8 Hz, 3.8 Hz), 4.09-4.12 (m, 1H), 4.53 (d, 1H, J=6.0 Hz), 4.55 (d, 1H, J=6.0 Hz), 4.85 (s, 1H), 5.04 (s, 2H), 5.10 (d, 2H, J=10.2 Hz), 7.29-7.37 (m, 10H), 7.40 (br, 1H); $^{13}$C-NMR (150 MHz, DMSO-$d_6$ rotamers): δ4.11, 14.38, 15.30, 24.63, 26.25, 29.04, 37.21, 37.72, 51.89, 53.38, 54.35, 65.51, 65.91, 66.12, 83.20, 83.27, 83.73, 83.77, 84.83, 109.09, 109.22, 111.32, 111.35, 127.16, 127.26, 127.59, 127.72, 127.80, 127.89, 128.26, 128.38, 128.43, 136.93, 137.05, 137.24, 155.49, 156.18, 172.75, 172.81; MS (ESI) m/z: 651 [M+Na]$^+$; HRMS: calculated for $C_{33}H_{44}N_2O_{10}Na$ ([M+Na]$^+$; 651.2894. found 651.2905.

Synthesis of 10. To a stirred solution of 9 (0.2 mmol) in 20 mL dioxane was added 4 M aqueous hydrochloric acid (5 mL, 20 mmol) at ambient temperature. The resultant mixture was stirred at ambient temperature for additional 40 h. The reaction was then quenched with saturated aqueous $NaHCO_3$ at 0° C. and was concentrated under reduced pressure. The crude product was extracted with ethyl acetate (3×40 mL). The combined organic phase was dried with anhydrous $Na_2SO_4$. The corresponding crude triol product was obtained after removing volatile components under reduced pressure. The crude product was dissolved in 5 mL dry pyridine and cooled down to 0° C. Acetic anhydride (370 μL, 4 mmol) was then added. The resultant reaction mixture was stirred at 0° C. at ambient temperature overnight, and then concentrated under reduced pressure at ambient temperature. After adding saturated $NaHCO_3$ (30 mL), the residual mixture was extracted with ethyl acetate (3×40 mL). The combined organic phase was washed with brine, dried with anhydrous $Na_2SO_4$. After removing volatile solvents with ratovapor, the crude product was purified by silica gel chromatography (hexane:EtOAc=2:1 then 1:1) to yield the triacetate derivative of 10 as a 1'-anomeric mixture.

Triacetate 10b R=Et, 62% yield. $[\alpha]_D^{17.9}$+12.88 (c 0.94, $CHCl_3$); $^1$H-NMR (600 MHz, DMSO-$d_6$, 74° C.): δ 1.07 (t, 3H, 7.0 Hz), 1.56-1.62 (m, 3H), 1.64-1.69 (m, 2H), 1.98-2.05 (m, 1H), 2.00 (s, 3H), 2.04 (s, 3H), 2.07 (s, 3H), 3.07-3.11 (m, 1H), 3.16-3.21 (m, 1H), 3.61 (s, 3H), 3.92-3.94 (m, 1J), 4.01-4.05 (m, 1H), 4.05-4.07 (m, 1H), 5.04-5.09 (m, 5H), 5.26 (dd, 1H, J=5.1 Hz, 1.2 Hz), 6.02 (d, 1H, J=1.2 Hz), 7.29-7.32 (m, 1H), 7.33-7.37 (m, 10H); $^{13}$C-NMR (150 MHz, DMSO-$d_6$ rotamers): δ4.11, 15.16, 20.24, 20.27, 20.36, 20.85, 27.75, 27.86, 29.09, 37.24, 37.63, 51.89, 53.57, 65.52, 65.99, 66.07, 73.58, 73.70, 73.95, 78.65, 78.84, 98.11, 127.27, 127.76, 127.79, 128.89, 128.31, 128.38, 128.43, 136.94, 137.01, 137.16, 155.38, 156.17, 168.97, 169.35, 169.62, 172.62, 172.69; MS (ESI) m/z: 723 [M+Na]$^+$; HRMS: calculated for $C_{35}H_{44}N_2O_{13}Na$ ([M+Na]$^+$) 723.2741. found: 723.2770.

Synthesis of 12. To an oven-dried flask was added $N^6$-benzoyladenine (44 mg, 0.18 mmol), hexamethyldisilazane (3 mL) and then dry pyridine (1 mL). The suspension was heated to 115° C. under argon to give a clear solution, which was stirred to 115° C. for additional 3 h. After removing volatile components to dryness, the residual volatile component was then coevaporated with toluene (3×5 mL). The mixture was subject to high vacuum for another 2 h. The resultant white solid was added to the solution of the triacetate derivative 10 as prepared above (0.037 mmol) and then dissolved in dry 1,2-dichloroethane (15 mL). The resultant suspension was treated with TMSOTf (33 μL, 0.18 mmol) dropwise under argon. The reaction mixture was heated at 50° C. for 2 h, cooled down to ambient temperature, and then quenched with saturated aqueous $NaHCO_3$ (20 mL). The organic phase was separated, and the aqueous phase was further extracted with $CH_2Cl_2$ (3×20 mL). The organic phase was combined, washed with brine and the dried with anhydrous $Na_2SO_4$. After removing volatile components with ratovapor, the crude product was purified by silica gel chromatography ($CH_2Cl_2$:MeOH=25:1) to give 12.

12b R=Et, 81% yield. $[\alpha]_D^{17.7}$+9.4 (c 0.86, $CHCl_3$); $^1$H-NMR (600 MHz, DMSO-$d_6$, 74° C.): δ 1.09 (t, 3H, J=7.1 Hz), 1.54-1.57 (m, 2H), 1.61-1.66 (m, 2H), 1.99-2.03 (m, 1H), 2.02 (s, 3H), 2.10-2.16 (m, 1H), 2.14 (s, 3H), 3.11 (q, 1H, J=7.1 Hz), 3.18 (q, 1H, J=7.1 Hz), 3.59 (s, 3H), 3.92-3.94 (m, 1H), 4.03-4.07 (m, 2H), 5.03-5.10 (m, 4H), 5.45 (t, 1H, J=7.2 Hz), 6.06 (t, 1H, J=5.4 Hz), 6.25 (d, 1H, J=5.4 Hz), 7.27-7.35 (m, 11H), 7.54 (t, 2H, J=7.7 Hz), 7.63 (t, 1H, J=7.4 Hz), 8.05 (d, 2H, J=7.5 Hz), 8.63 (s, 1H), 8.73 (s, 1H), 10.85 (br, 1H); $^{13}$C-NMR (150 MHz, DMSO-$d_6$ rotamers): δ 14.00, 14.23, 15.18, 20.28, 20.43, 23.72, 24.31, 27.79, 28.26, 28.73, 29.06, 29.12, 30.73, 31.32, 35.54, 35.95, 36.23, 51.87, 53.61, 65.50, 65.97, 71.95, 73.25, 73.32, 79.07, 79.25, 85.76, 85.88, 126.07, 127.13, 127.30, 127.56, 127.75, 127.83, 128.19, 128.27, 128.35, 128.44, 128.53, 128.56, 132.58, 133.25, 136.83, 136.95, 137.17, 143.82, 143.97, 150.73, 151.79, 151.89, 155.42, 156.12, 165.68, 169.42, 169.59, 172.60, 172.67; MS (ESI) m/z: 902 [M+Na]$^+$; HRMS: calculated for $C_{45}H_{50}N_7O_{12}$ ([M+H]$^+$) 880.3517. found: 880.3541.

Synthesis of 100, 101 and 110. To a stirred solution of 12 (0.02 mmol) in methanol (10 mL) was added potassium carbonate (14 mg, 0.1 mmol). The resultant mixture was stirred at ambient temperature for 8 h, concentrated to dryness and then redissolved in 10 mL water. To the mixture was added hydrazine monohydrate (5 μL, 0.1 mmol). The reaction was stirred for 8 h at ambient temperature, neutralized with 1M aqueous HCl and then concentrated under reduced pressure. This mixture was then dissolved in 6 mL ethanol:water (5:1). To this solution was added 20 μL acetic acid and palladium on activated carbon (15 mg, 10 wt %, wet Degussa type). The subsequent hydrogenation reaction was carried out with hydrogen balloon for 12 h. The reaction mixture was filtered through a short pad of Celite that was pre-washed with 20 mL MeOH and then 20 mL 0.1% TFA/water. The combined filtrates were concentrated under reduced pressure. The resultant crude product was purified by preparative reversed-phase HPLC (XBridge™ Prep C 18 5 μm OBD™ 19×150 mm) as the following: the 0-10% gradient of acetonitrile in aqueous trifluoroacetic acid (0.1%) in 10 min and a flow rate of 10 mL/min; The fractions containing desired compound was collected. The volatile solvents were removed by SpeedVac. The resultant solution was lyophilized to give the desired products 100, 101 and 110.

100 R=Et, 56% yield. $^1$H-NMR (600 MHz, MeOD): δ 1.11 (t, 3H, J=7.2 Hz), 1.93-1.97 (m, 2H), 1.99-2.07 (m, 2H), 2.23-2.27 (m, 2H), 2.28-2.32 (m, 1H), 3.05 (q, 2H, J=7.2 Hz), 3.46-3.48 (m, 1H), 3.97 (t, 1H, J=6.0 Hz), 4.19-4.22 (m, 1H), 4.37 (t, 1H, J=6.0 Hz), 4.70 (dd, 1H, J=5.4 Hz, 3.8 Hz), 5.99 (d, 1H, J=3.8 Hz), 8.30 (s, 2H); $^{13}$C-NMR (150 MHz, MeOD): δ 11.53, 26.99, 27.71, 33.51, 41.92, 53.75, 56.89, 74.57, 75.17, 80.91, 91.78, 118.09 (q, J=289.2 Hz), 121.12, 142.79, 150.26, 151.64, 156.02, 162.70 (q, J=35.4 Hz), 171.77; MS (ESI) m/z: 410 [M+H]$^+$; HRMS: calculated for $C_{17}H_{28}N_7O_5$ ([M+H]$^+$) 410.2152. found 410.2142.

101 R=Me, 52% yield. $^1$H-NMR (600 MHz, MeOD): δ1.96-2.03 (m, 2H), 2.05-2.08 (m, 2H), 2.25-2.29 (m, 2H), 2.64 (s, 3H), 3.43-3.45 (m, 1H), 3.99-4.03 (m, 1H), 4.19-4.22 (m, 1H), 4.36 (t, 1H, J=5.9 Hz), 4.65 (dd, 1H, J=5.4 Hz, 3.7 Hz), 6.01 (d, 1H, J=3.7 Hz), 8.35 (s, 1H), 8.36 (s, 1H); $^{13}$C-NMR (150 MHz, MeOD): δ 26.54, 27.60, 31.43, 33.55, 53.59, 58.23, 74.86, 75.01, 80.92, 91.85, 117.99 (q, J=289.7 Hz), 121.15, 143.44, 149.45, 150.10, 154.64, 162.57 (q, J=35.5 Hz), 171.52; MS (ESI) m/z: 396 [M+H]$^+$; HRMS: calculated for $C_{17}H_{28}N_7O_5$ ([M+H]$^+$) 396.1995. found: 396.1982.

110 R=Bn, 30% yield. $^1$H-NMR (600 MHz, MeOD): δ 1.97-2.10 (m, 4H), 2.31 (ddd, 1H, J=15.8 Hz, 5.8 Hz, 3.2 Hz), 2.40-2.45 (m, 1H), 3.57-3.59 (m, 1H), 3.99 (t, 1H, J=6.0 Hz), 4.12 (d, 1H, J=13.0 Hz), 4.20 (d, 1H, J=13.0 Hz), 4.41 (t, 1H, J=6.0 Hz), 4.70 (dd, 1H, J=5.8 Hz, 4.0 Hz), 5.49 (s, 2H), 5.99 (d, 1H, J=3.8 Hz), 7.10 (d, 2H, J=7.2 Hz), 7.23 (t, 2H, J=7.2 Hz), 7.31 (t, 1H, J=7.2 Hz), 8.20 (s, 1H), 8.33 (s, 1H); $^{13}$C-NMR (150 MHz, MeOD): δ 27.09, 27.87, 32.45, 53.71, 54.96, 57.08, 74.33, 74.84, 80.89, 91.88, 121.22, 130.22, 130.55, 130.68, 132.26, 142.88, 150.14, 151.49, 155.86, 162.55 (q, J=35.4 Hz), 171.75; MS (ESI) m/z: 472 [M+H]$^+$; HRMS: calculated for $C_{22}H_{30}N_7O_5$ ([M+H]$^+$) 472.2308. found 472.2299.

Synthesis of 13. A stream of ozone was bubbled through a stirred solution of the alkene 4 (0.64 mmol) in a 30 mL mixture of 1:1 methanol and $CH_2Cl_2$ at −78° C. until blue color persisted over 5 min. Then the solution was flushed with argon until it became clear, dimethyl sulfide (1 mL) was added into the solution at −78° C. After removing the dry ice bath, the reaction mixture was allowed to warm up spontaneously at ambient temperature and was then stirred overnight. Evaporation of the volatile chemicals under reduced pressure gave the crude acetal, which was purified by flash silica gel chromatography (hexane:EtOAc=2:1 then 1:1) to yield Compound 13 as colorless oil (215 mg, 77% yield).

13 [α]$_D^{16.6}$−7.2 (c 1.14, CHCl$_3$); $^1$H-NMR (500 MHz, CDCl$_3$): δ1.31 (s, 3H), 1.48 (s, 3H), 1.72-7.74 (m, 1H), 1.76-1.81 (m, 1H), 1.84-1.86 (m, 2H), 3.30 (s, 3H), 3.33 (s, 3H), 3.36 (s, 3H), 3.98-4.02 (m, 1H), 4.32 (dd, 1H, J=10.6 Hz, 3.6 Hz), 4.47 (t, 1H, J=5.5 Hz), 4.55 (d, 1H, J=5.9 Hz), 4.60 d, 1H, J=5.9 Hz), 4.97 (s, 1H), 5.10 (d, 1H, J=1.4 Hz), 5.18 (d, 1H, J=9.2 Hz), 7.31-7.36 (m, 5H); $^{13}$C-NMR (125 MHz, CDCl$_3$): δ24.97, 26.47, 37.78, 39.82, 45.90, 52.65, 53.46, 55.32, 66.52, 83.87, 84.57, 85.44, 102.45, 110.09, 112.35, 128.02, 128.08, 128.46, 136.69, 155.82; MS (ESI) m/z: 462 [M+Na]$^+$; HRMS: calculated for $C_{22}H_{33}NO_8Na$ ([M+Na]$^+$) 462.2104. found 462.2089.

Compound 14 was synthesized through the procedure for intermediate 4 using allyl iodide.

56% yield. [α]$_D^{17.5}$+7.8 (c 1.93, CHCl$_3$); $^1$H-NMR (500 MHz, CDCl$_3$): δ1.31 (s, 3H), 1.48 (s, 3H), 1.72-7.74 (m, 1H), 1.76-1.81 (m, 1H), 1.84-1.86 (m, 2H), 3.30 (s, 3H), 3.33 (s, 3H), 3.36 (s, 3H), 3.98-4.02 (m, 1H), 4.32 (dd, 1H, J=10.6 Hz, 3.6 Hz), 4.47 (t, 1H, J=5.5 Hz), 4.55 (d, 1H, J=5.9 Hz), 4.60 d, 1H, J=5.9 Hz), 4.97 (s, 1H), 5.10 (d, 1H, J=1.4 Hz), 5.18 (d, 1H, J=9.2 Hz), 7.31-7.36 (m, 5H); $^{13}$C-NMR (125 MHz, CDCl$_3$): δ24.97, 26.47, 37.78, 39.82, 45.90, 52.65, 53.46, 55.32, 66.52, 83.87, 84.57, 85.44, 102.45, 110.09, 112.35, 128.02, 128.08, 128.46, 136.69, 155.82; MS (ESI) m/z: 502 [M+Na]$^+$; HRMS: calculated for $C_{25}H_{37}NO_8Na$ ([M+Na]$^+$) 502.2417. found 502.2404.

Synthesis of 15. A solution of the acetal 14 (170 mg, 0.36 mmol) and iodine (9 mg, 0.035 mmol) in 15 mL acetone (ACS reagent, ≤0.5% $H_2O$) was stirred at room temperature for 20 min. The reaction process was carefully monitored by TLC($CH_2Cl_2$/MeOH=15:1). When most of the starting material (~90%) was consumed, the reaction was quenched with 5% aqueous $Na_2S_2O_3$ (5 mL). The reaction mixture was concentrated under reduced pressure and then diluted with 50 mL ethyl acetate. The mixture was washed with 20 mL $H_2O$ and then 20 mL brine. The resultant organic layer was dried with anhydrous $Na_2SO_4$. The solvent was removed to give the crude aldehyde. Without further purification, the aldehyde product was reduced with NaBH$_4$ as described for 5. After flash chromatography workup (hexane:EtOAc=1:1 then 1:2), 15 was obtained in 79% yield (12 mg acetal 7 was recovered).

15 [α]$_D^{17.5}$+14.7 (c 1.08, CHCl$_3$); $^1$H-NMR (600 MHz, DMSO-d$_6$ at 74° C.): 1.25 (s, 3H), 1.38 (s, 3H), 1.60-1.65 (m, 2H), 1.80-1.85 (m, 1H), 1.88-1.92 (m, 1H), 3.27 (s, 3H), 3.38 (q, 2H, J=6.0 Hz), 3.77 (dt, 1H, J=6.2 Hz, 1.2 Hz), 3.79 (dt, 1H, J=6.2 Hz, 1.2 Hz), 4.01 (dd, 1H, J=10.4 Hz, 4.2 Hz), 4.05 (br, 1H), 4.08 (t, 1H, J=4.8 Hz), 4.51 (d, 1H, J=6.0 Hz), 4.54 (d, 1H, J=6.0 Hz), 4.85 (s, 1H), 5.08 (dd, 1H, J=10.2 Hz, 1.4 Hz), 5.10 (s, 2H), 5.17 (dd, 1H, J=17.2 Hz, 1.2 Hz), 5.83-5.89 (m, 1H), 7.30-7.31 (m, 1H), 7.34-7.37 (m, 4H); $^{13}$C-NMR (150 MHz, DMSO-d$_6$ rotamers): δ 25.08, 26.60, 36.09, 37.81, 55.56, 58.90, 67.64, 76.97, 77.23, 77.48, 83.75, 84.55, 85.68, 110.16, 112.44, 117.54, 128.00, 128.20, 128.66, 135.18, 136.62, 156.54, 157.39; MS (ESI) m/z: 458 [M+Na]$^+$; HRMS: calculated for $C_{23}H_{33}NO_7Na$ ([M+Na]$^+$) 458.2155. found 458.2156.

Compound 16 was obtained from 15 by a series of steps analogous to steps 5→12 of Scheme 1.

16 98% yield. [α]$_D^{17.7}$+4.90 (c 1.15, CHCl$_3$); $^1$H-NMR (600 MHz, DMSO-d$_6$, 64° C.): δ 1.52-1.54 (m, 2H), 1.62-1.65 (m, 2H), 1.99-2.06 (m, 1H), 2.03 (s, 3H), 2.10-2.16 (m, 1H), 2.11 (s, 3H), 3.59 (s, 3H), 3.69 (dd, 1H, J=15.8 Hz, 6.4 Hz), 3.81 (dd, 1H, J=15.8 Hz, 6.4 Hz), 4.03-4.09 (m, 3H), 5.03-5.09 (m, 5H), 5.14 (d, 1H, J=17.2 Hz), 5.44 (t, 1H, J=5.2 Hz), 5.80-5.87 (m, 1H), 6.07 (t, 1H, J=5.6 Hz), 6.25 (d, 1H, J=5.5 Hz), 7.28-7.35 (m, 10H), 7.42 (br, 1H), 7.55 (t, 2H, J=7.9 Hz), 7.64 (t, 1H, J=7.4 Hz), 8.05 (d, 2H, J=7.4 Hz), 8.64 (s, 1H), 8.74 (s, 1H), 10.93 (s, 1H); $^{13}$C-NMR (150 MHz, DMSO-d$_6$ rotamers): δ 20.23, 20.37, 27.71, 28.98, 30.68, 35.53, 51.82, 53.55, 65.48, 66.19, 66.26, 71.97, 73.09, 73.20, 79.15, 85.71, 85.83, 116.89, 126.02, 127.09, 127.29, 127.71, 127.80, 128.16, 128.31, 128.48, 128.51, 132.52, 133.25, 136.70, 136.92, 143.73, 143.89, 150.70, 151.77, 151.85, 155.63, 156.08, 165.64, 169.35, 169.47, 172.61; MS (ESI) 914 [M+Na]$^+$; HRMS: calculated for $C_{46}H_{50}N_7O_{12}$ ([M+H]$^+$) 892.3517. found: 892.3495.

Compound 102 was obtained from 16 by the procedure described for conversion of 12 to 100 above and in Scheme 1.

102 $^1$H-NMR (500 MHz, MeOD): δ 0.83 (t, 3H, J=7.4 Hz), 1.42-1.49 (m, 1H), 1.52-1.59 (m, 1H), 1.94-2.09 (m, 4H), 2.21-2.26 (m, 1H), 2.29-2.35 (m, 1H), 2.92 (t, 2H, J=8.0 Hz) 3.44-3.48 (m, 1H), 4.01 (t, 1H, J=6.0 Hz), 4.19-4.22 (m, 1H), 4.40 (t, 1H, J=6.0 Hz), 4.67 (dd, 1H, J=5.4 Hz, 3.4 Hz), 6.02 (d, 1H, J=3.4 Hz), 8.35 (s, 1H), 8.36 (s, 1H); $^{13}$C-NMR (150 MHz, MeOD): δ 11.20, 20.77, 27.05, 27.64, 33.32, 48.23, 53.54, 57.29, 74.83, 75.16, 80.91, 91.90, 117.92 (q, J=289.4 Hz), 121.11, 143.47, 149.35, 150.09, 154.55, 162.44 (q, J=35.8 Hz), 171.50; MS (ESI) m/z: 424 [M+H]$^+$; HRMS: calculated for $C_{18}H_{30}N_7O_5$ ([M+H]$^+$) 424.2308. found 424.2296.

The synthesis of 23 (as shown in Scheme 6). To a solution of oxazolidinone 1 (2.0 g, 4.5 mmol) in dry diethyl ether (60 mL) was added anhydrous ethanol (316 μL, 5.4 mmol) and LiBH$_4$ (2.0M in THF, 2.7 mL, 5.4 mmol) at 0° C. The reaction was stirred for 30 min and allowed to warm to room temperature and stirred for additional 3 h under argon. The reaction was quenched slowly with aqueous sodium hydroxide (1.0M, 40 mL) and allowed to stir until both layers were clear. The aqueous phase was separated and extracted with ethyl acetate (40 mL×3). All the organic layers were combined, washed with brine and dried over MgSO$_4$. After the removal of organic solvent, the residue was purified by flash silica gel chromatography (hexane:EtOAc=2:1) to give an intermediate alcohol as a colorless oil (1.0 g, 3.68 mmol, 82% yield).

$^1$H-NMR (500 MHz, CDCl$_3$): δ 1.30 (s, 3H), 1.47 (s, 3H), 1.53-1.58 (m, 1H), 1.61-1.67 (m, 1H), 1.82-1.87 (m, 2H), 2.08-2.14 (m, 1H), 2.16-2.22 (m, 1H), 3.35 (s, 3H), 3.62 (dd, 2H, J=7.9 Hz, 5.0 Hz), 4.32 (dd, 1H, J=10.0 Hz, 5.3 Hz), 4.52 (d, 1H, J=5.9 Hz), 4.60 (d, 1H, J=5.9 Hz), 4.93 (s, 1H), 5.01-5.08 (m, 2H), 5.74-5.81 (m, 1H); $^{13}$C-NMR (125 MHz, CDCl$_3$): δ 24.98, 26.52, 35.90, 36.02, 37.38, 55.32, 64.42, 76.78, 77.03, 77.28, 84.69, 84.88, 85.45, 109.95, 112.29, 116.63, 136.55; MS (ESI) m/z: 295 ([M+Na]+; HRMS: calculated for C14H24NO5Na ([M+Na]+) 295.1521. found 295.1529.

To the solution of alcohol (600 mg, 2.2 mmol) in dichloromethane (30 mL) was added NaHCO$_3$ (1.8 g, 22 mmol) and Dess-Martin periodinane (1,1,1-triacetoxy-1,1-dihydro-1,2-benziodoxol-3(1H)-one) (1.12 g, 2.64 mmol) at 0° C. The suspension was stirred for 40 min at room temperature under nitrogen. The solution of Na$_2$S$_2$O$_3$ (2.0M, 2 mL) and saturated aqueous NaHCO$_3$ solution (10 mL) was added to above suspension and stirred for 15 min. The system was diluted with water (20 mL) and separated. The aqueous phase was extracted with dichloromethane (30 mL×3). All the organic layers were combined and washed with brine and dried over Na2SO4. After the concentration on rotavapor at room temperature, the crude aldehyde 22 was used to next run directly (Note: the concentrated aldehyde may decompose over time at room temperature).

The aldehyde 22 was dissolved in dry 1,2-dichloroethane (20 mL) and benzylamine (252 μL, 2.3 mmol), and sodium triacetoxyborohydride (653 mg, 3.1 mmol) were added in turn. The suspension was stirred at room temperature under a nitrogen atmosphere for 2 hours. TLC analysis showed the reaction had completed. The reaction mixture was quenched by adding aqueous saturated NaHCO$_3$ (20 mL). After the separation, the aqueous phase was extracted with dichloromethane (30 mL×3). The combined organic solvent was washed with brine and dried over MgSO$_4$. The crude compound was obtained after concentration, redissoved in THF (25 mL) and cooled down to 0° C. Saturated NaHCO$_3$ (5 mL) was added to above solution followed by benzyl chloroformate (400 μL, 3.3 mmol). The suspension was allowed to warm to room temperature spontaneously and stirred for 12 h. The mixture was diluted with water (30 mL) and extracted with ethyl acetate (40 mL×3). The combined organic layers were washed with brine, then dried over anhydrous Na$_2$SO$_4$ and evaporated. The residue was purified by silica gel chromatography (hexane:EtOAc=4:1~2:1) to furnish compound 23 as colorless oil (671 mg, 61% over 3 steps)

Compound 23 $[α]_D^{18.6}$–13.6 (c 0.98, CHCl$_3$); $^1$H-NMR (600 MHz, DMSO-d$_6$, 74° C.): δ 1.26 (s, 3H), 1.37 (s, 3H), 1.38-1.42 (m, 1H), 1.48-1.52 (m, 1H), 3.20-3.24 (m, 2H), 3.22 (s, 3H), 4.08 (t, 1H, J=7.5 Hz), 4.38 (d, 1H, J=5.8 Hz), 4.48 (d, 2H, J=2.3 Hz), 4.50 (d, 1H, J=5.8 Hz), 4.84 (s, 1H), 4.96-4.99 (m, 2H), 5.13 (s, 1H), 5.67-5.72 (m, 2H), 7.23-7.27 (m, 3H), 7.30-7.34 (m, 7H); $^{13}$C-NMR (150 MHz, DMSO-d6 rotamers): δ 24.72, 26.30, 32.78, 33.02, 36.25, 49.74, 50.02, 50.21, 50.42, 54.47, 65.39, 66.38, 66.55, 83.64, 83.94, 84.04, 84.77, 84.83, 108.95, 111.31, 11672, 116.86, 127.01, 127.10, 127.16, 127.48, 127.68, 127.78, 127.83, 128.29, 128.37, 128.48, 128.51, 136.10, 136.26, 136.86, 138.15, 155.90, 156.11; MS (ESI) m/z: 518 ([M+Na]$^+$); HRMS: calculated for C29H37NO6Na ([M+Na]$^+$) 518.2519. found 518.2522.

Compounds 201 and 202 were synthesized from intermediate 23, via intermediate 24, as shown in Scheme 6.

Compound 201 $^1$H-NMR (500 MHz, D$_2$O): δ 1.49-1.55 (m, 2H), 1.84-1.97 (m, 5H), 2.96 (dd, 1H, J=12.8 Hz, 6.9 Hz), 3.05 (dd, 1H, J=12.8 Hz, 5.4 Hz), 3.82 (t, 1H, J=6.0 Hz), 3.99-4.03 (m, 1H), 4.19-4.22 (m, 1H), 4.36 (t, 1H, J=5.9 Hz), 4.65 (dd, 1H, J=5.4 Hz, 3.7 Hz), 6.01 (d, 1H, J=3.7 Hz), 8.35 (s, 1H), 8.36 (s, 1H); $^{13}$C-NMR (150 MHz, D$_2$O): δ 25.84, 26.88, 33.12, 33.65, 41.94, 53.79, 73.35, 81.18, 88.81, 115.28, 116.25 (q, J=289.8 Hz), 119.02, 142.76, 144.67, 148.17, 150.08, 162.97 (q, J=35.2 Hz), 173.33; MS (ESI) m/z: 396 [M+H]$^+$; HRMS: calculated for C$_{16}$H$_{25}$N$_7$O$_5$ ([M+H]$^+$) 396.1995. found: 396.1982.

Compound 202 $^1$H-NMR (600 MHz, MeOD): δ 1.46-1.56 (m, 2H), 1.76-1.80 (m, 1H), 1.83-1.91 (m, 2H), 1.92-2.03 (m, 2H), 2.94-3.00 (m, 1H), 3.82 (t, 1H, J=7.0 Hz), 3.95 (d, 1H, J=13.0 Hz), 3.98-4.00 (m, 1H), 4.04 (d, 1H, J=13.0 Hz), 4.08 (t, 1H, J=5.7 Hz), 4.49 (dd, 1H, J=5.4 Hz, 4.0 Hz), 5.84 (d, 1H, J=4.0 Hz), 7.12 (t, 2H, J=7.4 Hz), 7.20 (t, 2H, J=7.4 Hz), 7.25 (d, 1H, J=7.4 Hz), 8.09 (s, 1H), 8.16 (s, 1H); $^{13}$C-NMR (150 MHz, MeOD): δ 27.90, 28.72, 34.32, 34.69, 52.07, 53.01, 54.07, 74.88, 75.36, 82.07, 91.65, 121.19, 130.37, 130.83, 130.90, 132.10, 142.68, 150.18, 151.31, 162.40 (q, J=35.4 Hz), 171.94; MS (ESI) m/z: 486 [M+H]$^+$; HRMS: calculated for C$_{23}$H$_{32}$N$_7$O$_5$ ([M+H]$^+$) 486.2465. found: 486.2464.

The synthesis of 204.

Compound 31 (Scheme 8) was derived from intermediate 40 in a similar way to the preparation of compound 27 in scheme 7.

Compound 31 $[α]_D^{18.3}$–5.2 (c 0.93, CHCl$_3$); $^1$H-NMR (600 MHz, DMSO-d$_6$, 84° C.): δ 1.31-1.39 (m, 2H), 1.64-1.67 (m, 1H), 1.75-1.80 (m, 1H), 1.81-1.88 (m, 2H), 1.92-1.95 (m, 1H), 2.04 (s, 3H), 2.10 (s, 3H), 3.13-3.16 (m, 1H), 3.23-3.26 (m, 1H), 3.66 (s, 3H), 4.15-4.18 (m, 1H), 4.24-4.28 (m, 1H), 4.39 (d, 1H, J=15.6 Hz), 4.45 (d, 1H, J=15.6 Hz), 5.10 (d, 2H, J=5.5 Hz), 5.41 (t, 1H, J=5.6 Hz), 6.04 (t, 1H, J=5.6 Hz), 6.23 (d, 1H, J=5.6 Hz), 7.12-7.13 (m, 2H), 7.22-7.31 (m, 8H), 7.54 (t, 2H, J=7.6 Hz), 7.63 (t, 1H, J=7.4 Hz), 8.04 (d, 2H, J=7.6 Hz), 8.59 (s, 1H), 8.71 (s, 1H), 9.39 (d, 1H, J=6.4 Hz), 10.76 (s, 1H); $^{13}$C-NMR (150 MHz, DMSO-d$_6$ rotamers): δ 20.25, 20.38, 20.42, 26.70, 27.48, 30.72, 32.41, 32.81, 34.25, 52.29, 52.82, 54.94, 66.38, 66.52, 71.89, 73.17, 79.17, 85.75, 85.85, 115.77 (q, J=286.1 Hz), 126.01, 126.90, 127.12, 127.28, 127.39, 127.51, 127.79, 128.29, 128.32, 128.43, 128.52, 128.54, 132.57, 133.23, 136.77, 137.85, 143.88, 150.71, 151.80, 151.85, 155.87, 156.59 (q, J=36.4 Hz), 165.67, 169.40, 169.51, 169.60, 170.92; MS (ESI) m/z: 940 ([M+Na]$^+$; HRMS: calculated for C$_{45}$H$_{47}$N$_7$O$_{11}$F$_3$ ([M+Na]$^+$) 918.3286. found 918.3311.

A suspension of 20% palladium hydroxide on activated carbon (25 mg) in a solution of compound 31 (20 mg) in trifluoroethanol (10 mL) was stirred under hydrogen balloon at room temperature for 16 h. After this period, the mixture was filtered though a pad of Celite, which was washed with methanol (40 mL). The combined filtrates were concentrated and redissolved in dichloromethane (5 mL). 1,3-Di-Boc-2-methylisothiourea (8.2 mg, 0.028 mmol) and triethylamine (8 µL, 0.06 mmol) was added to above solution, followed by the solution of mercury(II) chloride (7 mg, 0.028 mmol) in THF (1004). The resulting clear solution was turned to cloudy after stirring at room temperature for approximately 15 min. The mixture was attired for additional 2 h and filtered through a short pad of Celite, and the Celite pad was washed with dichloromethane (30 mL). The combined filtrates were concentrated under reduced pressure give a residue which was chromatographed over silica gel (DCM:MeOH=30:1) to afford compound 33 (12 mg).

To the solution of compound 33 (12 mg) in methanol (5 mL) was added 0.2 M lithium hydroxide (1.2 mL). The resulting solution was stirred at room temperature overnight and then concentrated. The residue was dissolved in water (3 mL) and hydrazine monohydrate (3.1 µL) was added. The reaction mixture was stirred for 6 h at room temperature and water was removed by lyophilization. The residue was treated with 1.5 mL TFA:H2O (9:1) for 1 h at room temperature. After this period, the reaction system was diluted with water (10 mL), then freeze-fried. The residue of 204 was dissolved in water (2 mL) and purified as described for compound 100.

Compound 204 $^1$H-NMR (500 MHz, MeOD): δ 1.58-1.62 (m, 2H), 1.88-2.06 (m, 5H), 3.20 (t, 1H, J=1.8 Hz), 3.94 (t, 1H, J=5.8 Hz), 4.11-4.15 (m, 1H), 4.25 (t, 1H, J=5.7 Hz), 4.75 (dd, 1H, J=5.4 Hz, 4.0 Hz), 6.00 (d, 1H, J=4.0 Hz), 8.30 (s, 1H), 8.31 (s, 1H); MS (ESI) m/z: 438 [M+H]$^+$; HRMS: calculated for $C_{17}H_{28}N_9O_5$ ([M+H]$^+$) 438.2213. found: 438.2210.

Synthesis of 300 as depicted in Scheme 13: To the solution of alkene (100 mg, 021 mmol) and protected vinyl glycine (100 mg, 0.42 mmol) in dry dichloromethane (20 mL) was added Grubbs 2$^{nd}$ catalyst (35 mg, 0.041 mmol) under argon. The resulting dark brown solution was sealed and heated to reflux for 6 hr and cooled down to room temperature. The system was concentrated and purified through silica gel column (hexane:EA=4:1 to 3:1) to yield cross coupling product 41 (60 mg, 41%). $^1$H NMR (CDCl$_3$, 500 MHz, rotamers): δ 1.27 (s, 3H), 1.46 (s, 3H), 1.62-1.64 (m, 1H), 1.78-1.82 (m, 0.4H), 2.00-2.10 (m, 0.6H), 2.14-2.17 (m, 0.4H), 2.20-2.24 (m, 0.6H), 2.28-2.38 (m, 1H), 3.21 (s, 1.3H), 3.30 (s, 1.7H), 3.70 (1.7H), 3.72 (s, 1.3H), 4.08-4.11 (m, 0.4H), 4.12-4.15 (m, 0.6H), 4.25-4.35 (m, 1.4H), 4.41 (d, 0.6H, J=5.0 Hz), 4.47 (d, 0.4H, J=5.0 Hz), 4.54 ((d, 0.6H, J=5.0 Hz), 4.63-4.71 (m, 2H), 4.87 (s, 0.4H), 4.92 (s, 0.6H), 5.10-5.23 (m, 5.5H), 5.37-5.44 (m, 1.5H), 7.26-7.35 (m, 15H); $^{13}$C NMR (CDCl$_3$, 600 MHz, rotamers): δ 14.40, 21.26, 25.02, 25.08, 26.60, 29.90, 52.75, 52.83, 55.37, 55.51, 55.60, 55.70, 60.61, 67.25, 67.76, 83.93, 84.03, 84.26, 84.39, 85.60, 85.65, 110.10, 110.28, 112.39, 112.47, 126.50, 127.62, 128.08, 128.16, 128.36, 128.42, 128.49, 128.66, 128.68, 128.73, 128.77, 131.56, 136.35, 136.64, 136.70, 138.56, 155.61, 155.67, 157.22, 171.38; MS (ESI): 703 ([M+H]$^+$)

The compound 37 was converted to its fully-protected form as previously described. HRMS: calculated for $C_{51}H_{52}N_7O_{12}$ ([M+H]$^+$) 954.3674. found 954.3672. The deprotection was carried out through hydrogenolysis and basic treatment to give the final compound 300. $^1$H-NMR (600 MHz, MeOD): δ 1.65-1.70 (m, 2H), 1.96-2.08 (m, 4H), 2.25-2.29 (m, 2H), 3.43-3.45 (m, 1H), 3.99-4.03 (m, 1H), 4.19-4.22 (m, 1H), 4.36 (t, 1H, J=5.9 Hz), 4.65 (dd, 1H, J=5.4 Hz, 3.7 Hz), 6.00 (d, 1H, J=3.7 Hz), 8.35 (s, 1H), 8.36 (s, 1H); MS (ESI): 396 ([M+H]$^+$); HRMS: calculated for $C_{16}H_{26}N_7O_5$ ([M+H]$^+$) 396.1995. found 396.1982.

The compounds described above were tested as described below:

Methylation Reaction. The 20 µL methylation reaction was carried out at ambient temperature using two mixtures: A. 10 µl of enzyme mixture in the assay buffer containing 50 mM Hepes (pH=8.0), 0.005% Tween-20, 5 µm/ml BSA and 1 mM TCEP; B. 10 µl of a mixture of 1.5 µM, 0.15 µCi [$^3$H-Me]-SAM cofactor and 3 µM of the corresponding peptide substrate in the same assay buffer. After A and B were mixed for a designated time period, the reaction mixture was examined with our filter-paper assay.

Conditions for the enzymes:

| Enzyme | [Enzyme mixture] (nM) | [Enzyme]$_{final}$ (nM) | Peptide Substrate | Reaction Time (h) |
|---|---|---|---|---|
| G9a (913-1913) | 40 | 20 | H3 (1-21 aa) | 1 |
| GLP1 (951-1235) | 20 | 10 | H3 (1-21 aa) | 1 |
| SUV39H2 (112-410) | 10 | 5 | H3 (1-21 aa) | 4 |
| SET7/9 Full-length | 300 | 150 | H3 (1-21 aa) | 3 |
| PRMT1 (10-352) | 200 | 100 | RGG | 1.5 |
| PRMT3 (211-531) | 200 | 100 | RGG | 3 |
| CARM1 (19-608) | 600 | 300 | H3 (1-40 aa) | 7 |
| SET8 (191-352) | 2000 | 1000 | H4 (10-30 aa) | 8 |
| SETD2 (1347-1711) | 500 | 250 | H3 (20-50 aa) | 4 |
| SMYD2 Full-length | 100 | 50 | p53 (360-393 aa) | 10 |

H3 (1-21-aa):
(SEQ ID NO: 1)
ARTKQTARKSTGGKAPRKQLA

RGG:
(SEQ ID NO: 2)
GGRGGFGGRGGFGGRGGFG

H3 (1-40 aa):
(SEQ ID NO: 3)
ARTKQTARKSTGGKAPRKQLATKAARKSAPATGGVKKPHR

H4 (10-30 aa):
(SEQ ID NO: 4)
LGKGGAKRHRKVLRDNIQGIT

H3 (20-50 aa):
(SEQ ID NO: 5)
ATKAARKSAPATGGVKKPHRYRPGTVALRE p53 (360-393 aa):
(SEQ ID NO: 6)
GGSRAHSSHLKSKKGQSTSRHKKLMFKTEGPDSD

Filter-paper Assay. This assay relies on Whatman P-81 filter paper, which binds peptides but not SAM. Protein Methyl Transferases (PMTS) transfer $^3$H-Me of [$^3$H-Me]-SAM to peptide substrates and the resultant $^3$H-methylated, filter-paper-bound peptide is quantified with a scintillation counter. Briefly, 6 μl of the methylation reaction was spotted onto Whatman P-81 phosphocellulose filter paper (1.2×1.2 cm$^2$) to immobilize the $^3$H-labeled peptide. After drying in air for 20 min, the filter paper was immersed into 20 mL of 50 mM Na$_2$CO$_3$/NaHCO$_3$ buffer (pH=9.2), and washed 5 times for 10 min each time. The washed filter paper was then transferred to a 20 ml scintillation vial containing 1 mL of distilled water and 10 mL of Ultima Gold scintillation cocktail or 7 mL scintillation vial containing 0.5 mL od distilled water and 5 mL of scintillation cocktail (PerkinElmer). The radioactivity was quantified by a Beckman LS6000IC liquid scintillation counter.

Dose-response Curves and IC$_{50}$. Twice the PMT concentration was incubated for 10 min with varied concentration of inhibitors (0.1-400 μM stocks), into which 10 μl of the PMT peptide substrate and radioactive cofactor (3 μM of the corresponding peptide and 1.5 μM, 0.15 μCi [$^3$H-Me]-SAM) were added. After incubating the reaction mixture for the respective reaction time, the conversion was quantified with the filter paper assay as described above. The inhibition was expressed as the percentage between the high control (no inhibition) and the low control (no enzyme) as follows: Percentage Inhibition=[(high control−reading)/(high control−low control)]×100%. Each experiment was performed in triplicate. The IC$_{50}$ values were obtained by fitting inhibition percentage versus inhibitor concentration using GraphPad Prism5 software.

Cellular Assay: HEK-293T cells were grown in DMEM plus 10% FBS and maintained in a humidified incubator set to 37° C., 5% CO$_2$. For assessment of the inhibitor effect, cells were plated in 6-well plate at a density of 0.5×10$^6$ cells/well in 2 mL of media. The following day the media was removed and replenish with 2 mL of increasing concentrations of PropylSinefungin up to 100 μM. Cell were harvested after 24 h and proceed to do the histone extraction (see below). 8 μg of the histones were separated on 18% Tris-HCl gels (BIO-RAD), transferred to 0.2 μM PVDF membranes and blotted with histone 3 lysine 36 tri-methyl antibody (Abcam) or H3 (Millipore) as a loading control.

Histone Extraction: The nuclear pellet and cytoplasm extract were obtained using the Cell Lytic™ NuCLEAR Extraction Kit (SIGMA). Then 40 μL of cold 0.2 M Sulfuric Acid were added and incubate overnight at 4° C. Then, the samples were centrifuge at 11000×g for 1 min and the supernatant containing the histones was collected. The concentration was measured using Quick Start™ Bradford 1× Dye Reagent (BIO-RAD).

The results are shown in the following table, in which S-adenosyl homocysteine (SAH) and sinefungin (SIN) are controls:

| Compd No. | G9a | GLP1 | SET7/9 | SET8 | SETD2 | PRMT1 | PRMT3 | SUV39 H2 | CARM1 | SMYD2-FL |
|---|---|---|---|---|---|---|---|---|---|---|
| SAH | 6.7 | 0.7 | >100 | >100 | 3.0 | 8.6 | 39.5 | 0.6 | 1.9 | ~50 |
| SIN | 18.9 | 32.0 | 1.1 | >100 | 28.4 | 1.0 | 28.2 | 4.6 | 0.5 | 0.2 |
| 100 | >500 | >500 | 1.7 | >100 | 8.2 | 55 | 37.9 | 95.7 | 1.4 | 0.2 |
| 101 | 164.6 | 373.7 | 1.4 | >100 | 125.2 | 83.9 | 76.2 | 43.2 | 1.7 | 0.5 |
| 102 | >100 | >100 | 2.2 | >100 | 0.8 | 9.5 | ~100 | 9.8 | 3.0 | 0.5 |
| 103 | >100 | >100 | 12.6 | >100 | 2.9 | >50 | ~70 | ~100 | 9.9 | 0.3 |
| 104 | 32 | >100 | 14.8 | >100 | 11.3 | 29.9 | 0.9 | 16 | 1.1 | 3.6 |
| 105 | >100 | >100 | 16.6 | >100 | 5.2 | 1.9 | 1.9 | 13.3 | 0.09 | TBD |
| 106 | >50 | 37.4 | 33.3 | >100 | ≤1.5 | 3.7 | TBD | 37.5 | 0.06 | TBD |
| 107 | >100 | >100 | >100 | >100 | >100 | >100 | >100 | >100 | ~50 | ~50 |
| 109 | >100 | >100 | 0.19 | >100 | 37 | 2 | 1.8 | 33 | 0.05 | 1.7 |
| 110 | >100 | >100 | >100 | >100 | 0.5 | >100 | 5.1 | >100 | 22.4 | 4 |
| 111 | >100 | >100 | >100 | >100 | 46.5 | >100 | 33 | >100 | ~80 | >100 |
| 116a | >100 | >100 | 0.7 | >100 | >100 | >100 | >100 | >100 | >100 | 2.5 |
| 116b | >100 | >100 | 0.2 | >100 | >100 | >100 | >100 | >100 | >100 | 3 |
| 116c | >100 | >100 | 0.4 | >100 | >100 | >100 | >100 | >100 | >100 | 3 |
| 116d | >100 | >100 | 1.1 | >100 | >100 | >100 | >100 | >100 | 61.4 | <0.5 |
| 116e | >100 | >100 | 10.3 | >100 | ~100 | >100 | 9.7 | >100 | 42 | 9 |
| 201 | >100 | >100 | 27.6 | >100 | 136.1 | 2.5 | 13.1 | 24.5 | 0.1 | <0.2 |
| 202 | >100 | >100 | >100 | >100 | 10.8 | 15.25 | 3.4 | 10.1 | 0.09 | 1.6 |
| 203 | ~25 | ~12.5 | 9.6 | 21.8 | 4.2 | >100 | 7.6 | 10.7 | 5.2 | 1 |
| 204 | 32 | 24.2 | 34.8 | >100 | 24.4 | 1.9 | 0.7 | 8.6 | 0.02 | 0.2 |
| 205 | >100 | >100 | >100 | >100 | 67.9 | ~50 | 9.4 | TBD | 32.7 | ~12.5 |
| 300 | ~100 | ~100 | ~70 | ~70 | 21.2 | 18.75 | 9.9 | 35.13 | 4.4 | 37 |

Compounds that show selective inhibition of one or a few families of PMTs are of greater interest as candidates for use in therapy, since it is believed that broad spectrum inhibition is likely to be associated with a higher probability of side effects. In this regard, compounds described above as 201, 202, 204, 109, 105 and 106 are of interest because of their apparent selectivity—among the subset of PMTs screened—for CARM1 inhibition. Analogously, the deazapurines (116a, 116b and 116c) appear to be selective for SET7/9.

Compound 102, which, along with 110, is selective for SETD2, was tested in vivo and showed activity in inhibiting histone methyltransferase.

The invention claimed is:

1. A compound of formula I or II

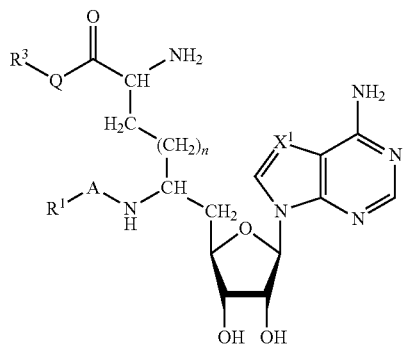

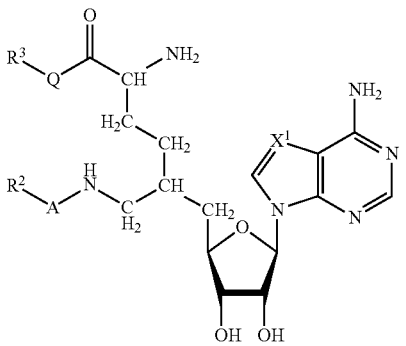

wherein:
$X^1$ is N or CH;
Q is NH or O;
A is chosen from direct bond, $(C_1-C_{20})$hydrocarbon, $(C_1-C_{20})$oxaalkyl and $(C_1-C_{20})$azaalkyl;
$R^1$ is chosen from —C(=NH)NH$_2$, —C(=NH)NH($C_1$-$C_{10}$)hydrocarbon, fluoro($C_1$-$C_6$)hydrocarbon, and —CH(NH$_2$)COOH, with the provisos that,
(1) when A is a direct bond, $R^1$ cannot be H;
(2) when QR$^3$ is OH, $R^1$ cannot be fluoro($C_2$-$C_6$)hydrocarbon; or
the combination $R^1$A is chosen from ethyl, propyl, isopropyl, butyl, s-butyl, t-butyl, cyclic hydrocarbon groups of from 3 to 8 carbon atoms, benzyl, phenethyl, cyclohexylmethyl, adamantyl, camphoryl and naphthylethyl;
$R^2$ is chosen from hydrogen, —C(=NH)NH$_2$, —C(=NH)NH($C_1$-$C_{10}$)hydrocarbon and —CH(NH$_2$)COOH;
$R^3$ is chosen from H and $(C_1-C_{20})$ hydrocarbon; and
n is 1 or 2.

2. A compound according to claim 1 wherein $R^3$ is chosen from H, methyl and ethyl.

3. A compound according to claim 1 wherein n is 2.

4. A compound according to claim 3 wherein QR$^3$ is OH.

5. A compound according to claim 1 of formula Ia or IIa

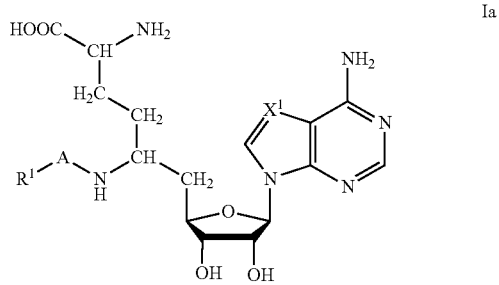

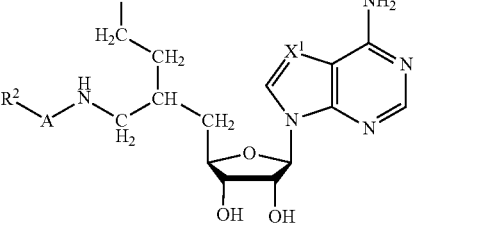

wherein:
$X^1$ is N or CH;
A is chosen from direct bond, $(C_1-C_{20})$hydrocarbon, $(C_1-C_{20})$oxaalkyl and $(C_1-C_{20})$azaalkyl;

R¹ is chosen from —C(=NH)NH₂, —C(=NH)NH(C₁-C₁₀)hydrocarbon, CF₃ and —CH(NH₂)COOH, with the proviso that, when A is a direct bond, R¹ cannot be H; or the combination R¹A is chosen from ethyl, propyl, isopropyl, butyl, s-butyl, t-butyl, cyclic hydrocarbon groups of from 3 to 8 carbon atoms, benzyl, phenethyl, cyclohexylmethyl, adamantyl, camphoryl and naphthylethyl;

R² is chosen from hydrogen, —C(=NH)NH₂, —C(=NH)NH(C₁-C₁₀)hydrocarbon and —CH(NH₂)COOH.

6. A compound according to claim 1 of formula I or Ia wherein R¹-A is chosen from ethyl, propyl, isopropyl, butyl, s-butyl, t-butyl, cyclic hydrocarbon groups of from 3 to 8 carbon atoms, benzyl and (C₃-C₆)oxaalkyl.

7. A compound according to claim 1 of formula I or Ia wherein R¹-A is chosen from amino(C₁-C₆)alkyl, benzylamino(C₁-C₆)alkyl and guanidino(C₁-C₆)alkyl.

8. A compound according to claim 1 of formula I or Ia wherein R¹-A is chosen from HOOC(NH₂)CH-azaalkyl and NH₂(NH=)C-azaalkyl.

9. A compound according to claim 1 of formula II or IIa wherein R²-A is chosen from hydrogen, (C₁-C₆)alkyl, benzyl and —C(=NH)NH₂.

10. A compound according to claim 1 wherein X¹ is N.

11. A compound according to claim 1 wherein X¹ is CH.

12. A method for inhibiting the activity of a G9a, GLP1, SET7/9, SET8, SETD2, PRMT1, PRMT3, SUV39H2, CARM1, or SMYD2-FL methyltransferase enzyme comprising bringing said methyltransferase enzyme into contact with a compound according to claim 1.

13. A pharmaceutical composition comprising a pharmaceutically acceptable carrier and a compound according to claim 1.

* * * * *

SEQUENCE LISTING

<160> NUMBER OF SEQ ID NOS: 6

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic peptide

<400> SEQUENCE: 2

Gly Gly Arg Gly Gly Phe Gly Gly Arg Gly Gly Phe Gly Gly Arg Gly
1               5                   10                  15

Gly Phe Gly

<210> SEQ ID NO 3
<211> LENGTH: 40
<212> TYPE: PRT
<213> ORGANISM: Artificial Sequence
<220> FEATURE:
<223> OTHER INFORMATION: Synthetic peptide

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg
        35                  40

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide

<400> SEQUENCE: 4

Leu Gly Lys Gly Gly Ala Lys Arg His Arg Lys Val Leu Arg Asp Asn
1               5                   10                  15

Ile Gln Gly Ile Thr
            20

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide

<400> SEQUENCE: 5

Ala Thr Lys Ala Ala Arg Lys Ser Ala Pro Ala Thr Gly Gly Val Lys

```
1               5                   10                  15
Lys Pro His Arg Tyr Arg Pro Gly Thr Val Ala Leu Arg Glu
            20                  25                  30

<210> SEQ ID NO 6
<211> LENGTH: 34
<212> TYPE: PRT
<213> ORGANISM: Artificial Sequence
<220> FEATURE:
<223> OTHER INFORMATION: Synthetic peptide

<400> SEQUENCE: 6

Gly Gly Ser Arg Ala His Ser Ser His Leu Lys Ser Lys Lys Gly Gln
1               5                   10                  15

Ser Thr Ser Arg His Lys Lys Leu Met Phe Lys Thr Glu Gly Pro Asp
            20                  25                  30

Ser Asp
```